United States Patent
Lockard et al.

(10) Patent No.: US 10,894,032 B2
(45) Date of Patent: Jan. 19, 2021

(54) MICROBIAL-RELIEF COMPOSITION

(71) Applicant: Curazene, LLC, McKinney, TX (US)

(72) Inventors: Ronald J. Lockard, McKinney, TX (US); Dominic G. Brown, McKinney, TX (US); James Pate, Little Rock, AR (US)

(73) Assignee: CURAZENE, LLC, McKinney, TX (US)

( * ) Notice: Subject to any disclaimer, the term of this patent is extended or adjusted under 35 U.S.C. 154(b) by 0 days.

(21) Appl. No.: 14/671,841

(22) Filed: Mar. 27, 2015

(65) Prior Publication Data

US 2015/0272925 A1    Oct. 1, 2015

Related U.S. Application Data

(60) Provisional application No. 61/971,861, filed on Mar. 28, 2014.

(51) Int. Cl.

| A61K 31/375 | (2006.01) |
|---|---|
| A61K 47/20 | (2006.01) |
| A61K 38/12 | (2006.01) |
| A61K 31/65 | (2006.01) |
| A61K 31/7036 | (2006.01) |
| A61K 31/7056 | (2006.01) |
| A61K 31/7034 | (2006.01) |
| A61K 9/00 | (2006.01) |
| A61K 47/12 | (2006.01) |
| A61K 47/22 | (2006.01) |
| A61K 31/675 | (2006.01) |

(52) U.S. Cl.
CPC .......... *A61K 31/375* (2013.01); *A61K 9/0014* (2013.01); *A61K 31/65* (2013.01); *A61K 31/675* (2013.01); *A61K 31/7034* (2013.01); *A61K 31/7036* (2013.01); *A61K 31/7056* (2013.01); *A61K 38/12* (2013.01); *A61K 47/12* (2013.01); *A61K 47/20* (2013.01); *A61K 47/22* (2013.01)

(58) Field of Classification Search
CPC .... A61K 31/375; A61K 9/0014; A61K 31/65; A61K 31/675; A61K 31/7034; A61K 31/7036; A61K 31/7056; A61K 38/12; A61K 47/12; A61K 47/20; A61K 47/22
See application file for complete search history.

(56) References Cited

U.S. PATENT DOCUMENTS

| 3,925,543 | A | * | 12/1975 | Donohue | A61K 8/43 424/52 |
|---|---|---|---|---|---|
| 6,294,186 | B1 | | 9/2001 | Beerse et al. | |
| 6,953,772 | B2 | * | 10/2005 | Lopes | C11D 3/042 134/41 |
| 7,001,592 | B1 | * | 2/2006 | Traynor | A61K 8/042 424/400 |
| 9,259,006 | B2 | * | 2/2016 | Lemons | A01N 37/02 |
| 2006/0062821 | A1 | | 3/2006 | Lopes | |
| 2006/0062832 | A1 | | 3/2006 | Lopes | |
| 2007/0232694 | A1 | | 10/2007 | Phillips | |
| 2007/0238630 | A1 | | 10/2007 | Phillips | |
| 2009/0214628 | A1 | * | 8/2009 | de Rijk | A01N 59/06 424/450 |
| 2010/0209472 | A1 | * | 8/2010 | Wang | A61K 31/337 424/423 |
| 2011/0207822 | A1 | * | 8/2011 | Lopes | A61K 9/0043 514/574 |
| 2011/0280853 | A1 | | 11/2011 | Fallon et al. | |
| 2012/0070518 | A1 | | 3/2012 | Wang et al. | |
| 2013/0197431 | A1 | * | 8/2013 | Wang | A61K 31/337 604/93.01 |
| 2015/0272969 | A1 | * | 10/2015 | Ahmed | A01N 37/02 514/159 |
| 2015/0342854 | A1 | * | 12/2015 | Shibuya | A61Q 19/08 424/62 |
| 2016/0263062 | A1 | * | 9/2016 | Liebowitz | A01N 37/36 |

FOREIGN PATENT DOCUMENTS

| CN | 102021085 A | 4/2011 | |
|---|---|---|---|
| CN | 102181325 A | 9/2011 | |
| GB | 2014848 A | 9/1979 | |
| WO | WO 2004073033 A2 * | 8/2004 | .......... A61K 9/5057 |
| WO | 2008031104 A2 | 3/2008 | |

(Continued)

OTHER PUBLICATIONS

Nakanishi T. A report on the therapeutical experiences of which have successfully made several antibiotics-resistant bacteria (MRSA etc) negative on bedsores and respiratory organs. Igaku Kenkyu. Sep. 1993;63(3):95-100. abstract.*

Cursino et al. Synergic interaction between ascorbic acid and antibiotics against Pseudomonas aeruginosa. Braz. arch. biol. technol., 2005, 48(3):379-384.*

Cursino et al. Synergic Interaction between Ascorbic Acid and Antibiotics against Pseudomonas aeruginosa. Brazilian Archives of Biology and Technology, 2005, 48(3):379-384. (Year: 2005).*

(Continued)

*Primary Examiner* — Robert A Wax
*Assistant Examiner* — Olga V. Tcherkasskaya
(74) *Attorney, Agent, or Firm* — Edwin S. Flores; Daniel J. Chalker; Chalker Flores, LLP

(57) ABSTRACT

The present invention includes an antimicrobial composition comprising a safe and effective amount of a surfactant, e.g., sodium dodecylbenzene sulfonate, a safe and effective amount of ascorbic acid; and optionally a safe and effective amount of an excipient, e.g., magnesium stearate. The composition may further comprise a safe and effective amount of an antibiotic, a safe and effective amount of stearic acid, a dermatologically acceptable cream compound, a chlorine compound, and/or an abrasion material.

12 Claims, 9 Drawing Sheets

(56) References Cited

FOREIGN PATENT DOCUMENTS

| WO | WO 2008031104 A2 * | 3/2008 | ............. A01N 37/02 |
| WO | WO 2008085446 A2 * | 7/2008 | ............. A01N 27/00 |

OTHER PUBLICATIONS

International Search Report, PCT/US2015/023158, dated Jun. 20, 2015, Issued by Australian Patent Office.

* cited by examiner

Day 1

Day 5

Figure 3a
Staph. aureus- zone of inhibition is 40mm
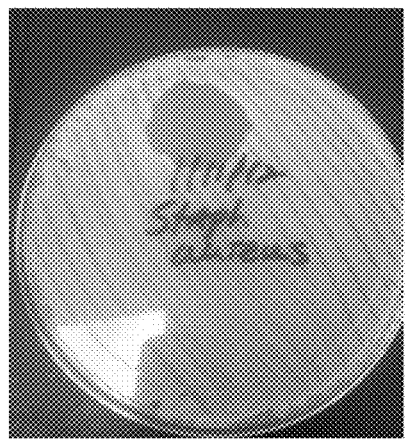
Figure 3b
MRSA- zone of inhibition is 36 mm
Figure 3c
| Test Sample | Zone of Inhibition in mm | | |
|---|---|---|---|
| | 21A | 21B | 21C |
| Pseudomonas aeruginose | 0 | 0 | 0 |
| MRSA | 39 | 27 | 28 |
| E.coli | 24 | 25 | 25 |
| Klebsiella pneumoniae | 29 | 27 | 30 |
| Enterococcus sp. | 26 | 39 | 25 |
| Acinetobacter baumannii | 24 | 25 | 25 |

Location of staph-infected wound

MICROBIAL-RELIEF COMPOSITION

CROSS-REFERENCE TO RELATED APPLICATIONS

This non-provisional Patent Application claims priority to U.S. Provisional Patent Application Ser. No. 61/971,861, filed Mar. 28, 2014, entitled "Microbial-Relief Composition," the contents of which is incorporated by reference herein in its entirety.

TECHNICAL FIELD OF THE INVENTION

The present invention relates in general to the field of anti-microbial compositions and skin cleansers comprising surfactants.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with a microbial-relief composition, methods and uses thereof.

U.S. Pat. No. 7,001,592, entitled Sunscreen compositions and methods of use, (filed Feb. 21, 2006 by Traynor, et al.) describes additives for addition to a bodywash that may also contain non-sunscreen active ingredients such as ascorbic acid, neomycin, and sodium dodecylbenzene sulfonate, which is listed as an example of a surfactant.

U.S. Pat. No. 6,294,186, entitled Antimicrobial compositions comprising a benzoic acid analog and a metal salt, (filed Sep. 25, 2001 by Beerse, et al.) describes antimicrobial compositions that provide enhanced immediate as well as residual anti-viral and antibacterial activity against gram-negative bacteria, gram-positive bacteria, viruses, and fungi. The compositions comprise a benzoic acid analog, a metal salt, and a dermatologically acceptable carrier.

U.S. Patent Application 2007/0238630, entitled Subcutaneous skin cleanser, (filed Mar. 29, 2006 by Douglas Howard Phillips) relates to a skin cleanser that is a combination of surfactant chemicals, chemicals that can cause gentle abrasion for the purpose of opening up the pathway from the skin surface, and chemicals that can change the molecular structure of a venom or toxin. The composition is said to be useful for cleansing the skin following exposure to poison ivy or following insect bites.

U.S. Patent Application 2007/0232694, entitled Skin cleanser, (filed Mar. 28, 2007 by Douglas Howard Phillips) relates to a skin cleanser that comprises an anionic surfactant and a hypochlorite salt, and optionally with an anionic dye and/or an abrasive.

U.S. Patent Application 2011/0280853, entitled Compositions and methods for treatment or prevention of *Staphylococcus aureus* infections and for the eradication or reduction of *Staphylococcus aureus* on surfaces, (filed Jan. 6, 2010 by Fallon et al.) relates to compositions that include one or more digestive enzymes, e.g., one or more proteases, lipases, and amylases.

SUMMARY OF THE INVENTION

The present invention includes in one embodiment an antimicrobial composition comprising: a safe and effective amount of sodium dodecylbenzene sulfonate surfactant at between 1 and 10% weight-to-weight; and a safe and effective amount of ascorbic acid, wherein the composition is antimicrobial. In one aspect, the composition further comprises a safe and effective amount of an antibiotic. In another aspect, the antibiotic is selected from at least one of bacitracin, bacitracin zinc, chlortetracycline hydrochloride, neomycin, clindamycin, erythromycin, or tetracycline hydrochloride. In another aspect, the surfactant is in a concentration of 2 to 4%, 0.5 to 2%, 2 to 10%, 4% to 8%, 5% to 9%, 1%, 2%, 3%, 4%, 5%, 6%, 7%, 8%, or 9% weight-to-weight. In another aspect, the composition further comprises a safe and effective amount of stearic acid from between a trace amount to 1% weight-to-weight and/or a dermatologically acceptable cream compound. In another aspect, the composition further comprises a biologically-compatible hypochlorite salt selected from the group consisting of sodium hypochlorite and calcium hypochlorite. In another aspect, the composition further comprises an abrasion material. In another aspect, the abrasion material is sodium carbonate, calcium carbonate, silicon dioxide or combinations thereof. In another aspect, the abrasion material is selected from the group consisting of sodium carbonate, sodium bicarbonate, calcium carbonate, sodium borate, silica, diatomaceous earth, cellulose-based materials, and combinations thereof. In another aspect, the composition is effective to kill gram positive bacteria or multiple drug resistant bacteria.

In another embodiment, the present invention includes an antimicrobial composition consisting essentially of a safe and effective amount of sodium dodecylbenzene sulfonate surfactant at between 1 and 10% weight-to-weight; a safe and effective amount of ascorbic acid; and a safe and effective amount of magnesium stearate, wherein the composition is antimicrobial. In one aspect, the composition further comprises a safe and effective amount of an antibiotic. In another aspect, the antibiotic is selected from at least one of bacitracin, bacitracin zinc, chlortetracycline hydrochloride, neomycin, clindamycin, erythromycin, or tetracycline hydrochloride. In another aspect, the e surfactant is in a concentration of 2 to 4%, 0.5 to 2%, 2 to 10%, 4% to 8%, 5% to 9%, 1%, 2%, 3%, 4%, 5%, 6%, 7%, 8%, or 9% weight-to-weight. In another aspect, the composition further comprises a safe and effective amount of stearic acid from between a trace to 1% weight-to-weight. In another aspect, the composition further comprises a dermatologically acceptable cream compound. In another aspect, the composition further comprises a biologically-compatible hypochlorite salt selected from the group consisting of sodium hypochlorite and calcium hypochlorite. In another aspect, the composition further comprises an abrasive material. In another aspect, the abrasive material is sodium carbonate, calcium carbonate, silicon dioxide or combinations thereof. In another aspect, the abrasive material is selected from the group consisting of sodium carbonate, sodium bicarbonate, calcium carbonate, sodium borate, silica, diatomaceous earth, cellulose-based materials, and combinations thereof. In another aspect, the composition is effective to kill gram positive bacteria or multiple drug resistant bacteria.

In another embodiment, the present invention includes a method to clean skin comprising: identifying a patient suspected of needing skin cleansing; and applying a skin cleanser, wherein the skin cleaner comprises: a safe and effective amount of a sodium dodecylbenzene sulfonate, at between 1 and 10% weight-to-weight; a safe and effective amount of ascorbic acid; and a safe and effective amount of magnesium stearate. In one aspect, the method further comprises adding a safe and effective amount of an antibiotic to the composition. In another aspect, the antibiotic is selected from at least one of bacitracin, bacitracin zinc, chlortetracycline hydrochloride, neomycin, clindamycin, erythromycin, or tetracycline hydrochloride. In another aspect, the surfactant is in a concentration of 2 to 4%, 0.5 to 2%, 2 to 10%, 4% to 8%, 5% to 9%, 1%, 2%, 3%, 4%, 5%, 6%, 7%, 8%, or 9% weight-to-weight. In another aspect, the method further comprises a safe and effective amount of stearic acid from between a trace to 1% weight-to-weight. In another aspect, the method further comprises a dermatologically acceptable cream compound. In another aspect, the method further comprises an abrasive material compound. In another aspect, the abrasive material compound is sodium carbonate, calcium carbonate, silicon dioxide or combinations thereof. In another aspect, the method further comprises repeating the step of applying a skin cleanser within 5 hours. In another aspect, the step of applying a skin cleanser within 5 hours further comprises cleaning a bacteria-infected lesion. In another aspect, the patient is a mammal. In another aspect, the patient is a human. In another aspect, the composition is effective to kill gram positive bacteria or multiple drug resistant bacteria.

BRIEF DESCRIPTION OF THE DRAWINGS

For a more complete understanding of the features and advantages of the present invention, reference is now made to the detailed description of the invention along with the accompanying figures and in which:

FIG. 1a, skin area at day 1: the area that is draining is 3 cm in diameter and the area of the Erythema was 4.5 cm in diameter. FIG. 1b shows the edges of the wound healing well and the over-all appearance of the wound is much improved.

FIG. 2a depicts the facial skin on day 1 before treatment. FIG. 3b depicts facial skin on day 5 after treatment.

FIGS. 3a to 3c shows the result of semi-quantitative in-vitro susceptibility testing by agar diffusion test. FIG. 3a shows *Staph. aureus*; the zone of inhibition is 40 mm. FIG. 3b shows Methicillin-resistant *Staphylococcus aureus* (MRSA); the zone of inhibition is 36 mm. FIG. 3c shows the results of agar diffusion test and lists the size of the zone of inhibition employing various microorganisms.

FIG. 4a shows the lesion one week after the lesion was first noticed. This photo was taken before treatment began with the composition of the present invention. FIG. 4b shows the wound 8 hours after first application of the composition. FIG. 4c shows the wound 12 hours after first application of the composition. FIG. 4d shows the wound 22 hours after first application of the composition. FIG. 4e shows the wound 24 hours after first application of the composition. FIG. 4f shows the wound with further improvement after application of the composition.

FIG. 5a shows the wound 5 days after first application of the composition of the present invention. FIG. 5b shows the wound 9 days after first application of the composition. FIG. 5c shows the wound 10 days after first application of the composition. FIG. 5d shows the wound 11 days after first application of the composition. FIGS. 5e and 5f show the wound with further improvement after application of the composition.

FIG. 6a shows the wound 16 days after first application of the composition of the present invention. FIG. 6b shows the wound 18 days after first application of the composition. FIG. 6c shows the wound 21 days after first application of the composition. FIG. 6d shows the wound 30 days after first application of the composition. FIG. 6e shows the wound 31 days after first application of the composition. FIG. 6f shows the wound 57 days after first application of the composition.

FIG. 7a shows the location of the staph-infected wound. FIG. 7b shows the wound before medical treatment. FIG. 7c shows the wound dressing being removed. FIG. 7d shows the wound having inflammation. FIG. 7e shows the first application of the composition. FIG. 7f shows the wound 12 hours after application of the composition.

FIG. 8a shows the wound with rapid improvement on day 1 after initiation of treatment. FIG. 8b shows the wound having better color appearance on day 2. FIG. 8c shows the wound with even better improvement on day 3. FIG. 8d shows the wound lacking inflamed color on day 6. FIG. 8e shows the wound before cleansing began with the composition of the present invention. FIG. 8f shows the wound the day cleansing began with the composition.

FIG. 9a shows the wound on Day 1. FIG. 9b shows the wound on Day 2. FIG. 9c shows the wound on Day 3. FIG. 9d shows the wound on Day 4. FIG. 9e shows the wound on Day 5. FIG. 9f shows the wound on Day 6.

DETAILED DESCRIPTION OF THE INVENTION

Figure 1A:
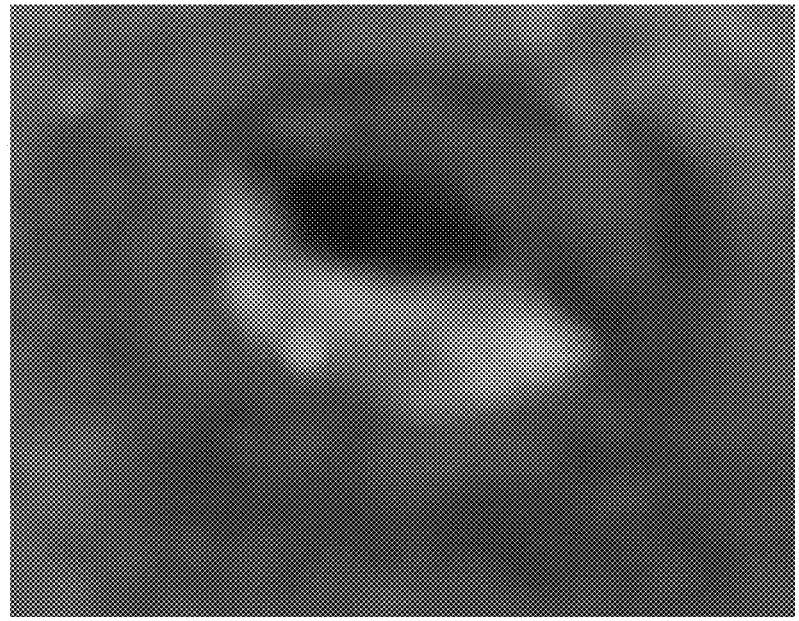
FIGS. 1a and 1b show photographs of Patient H, which were taken by the physician for documenting the progress of the treatment using a cosmetic embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity but include the general class of which a specific example may be used for illustration. The terminology herein is used to describe specific embodiments of the invention, but their usage does not delimit the invention, except as outlined in the claims.

Disclosed are compositions, for human use, with or without antibiotics, which can also be adapted for animal use, for infections and as safe and effective skin cleanser, ointment, serum, soap, or liquid formulated to kill bacteria, for example, gram positive bacteria or multiple drug resistant bacteria.

The skin cleanser that is capable of killing most bacteria in the infected area. The skin cleanser can be used on open wounds, cuts, scrapes and abrasions, help sanitize hands & reduce the spread of germs, and can be used on the entire surface. In one embodiment for treating or cleaning skin, the following ingredients (10 mL) are combined:

Neomycin sulfate (active) 10× Solution (1 mL) (Lot #10311203, CAT #685630, CAS #1405-10-3)

SDBS (Sodium Dodecylbenzene Sulfonate) Powder, 5× Solution (3.4 mL) (Lot #VG0860, CAT #D1064, CAS #25155-30-0, Spectrum Chemical MFG Corp, New Brunswick, N.J., $C_{18}H_{29}NaO_3S$)

A cream In one non-limiting example: Water, Ethylhexyl stearate, Emulsifying wax, Tocopheryl acetate, Aloe Barbadensis leaf juice, Disodium EDTA, Sorbitol, Cyclopentasiloxane, Methylchloroisothiazolinone and Methylisothiazolinone sold as: VERSABASE CREAM® PCCA (5.5 mL) (Professional Compounding Centers of America, Lot #2685467, CAT #30-3641

In another embodiment for treating or cleaning skin, the following ingredients (10 mL) are combined:

Neomycin sulfate, (active) 10× Solution (1 mL) (Lot #10311203, CAT #685630, CAS #1405-10-3)

SDBS (Sodium Dodecylbenzene Sulfonate) Powder, 5× Solution (3.4 mL) (Lot #VG0860, CAT #D1064, CAS #25155-30-0, Spectrum Chemical MFG Corp, New Brunswick, N.J., $C_{18}H_{29}NaO_3S$)

Base In one non-limiting example: Deionized water, glycerol, polysorbate 80, aloe barbadensis leaf juice, glycerin, white petrolatum, citric acid, trisodium citrate, germazide or other preservative, polysorbate, hydroxyethylcellulose, ascorbic acid, magnesium sulfate, stearic acid, tetrasodium EDTA, methylisothiazolinone.

In another embodiment for treating or cleaning skin, the following ingredients (10 mL) are combined:

Neomycin sulfate, (active) 10× Solution (1 mL) (Lot #10311203, CAT #685630, CAS #1405-10-3)

SDBS (Sodium Dodecylbenzene Sulfonate) Powder, 5× Solution (3.4 mL) (Lot #VG0860, CAT #D1064, CAS #25155-30-0, Spectrum Chemical MFG Corp, New Brunswick, N.J., $C_{18}H_{29}NaO_3S$)

Base In one non-limiting example: Deionized or U.S.P. water, Propylene glycol, polysorbate 80, glycerol monostearate, emulsifying wax, ascorbic acid, stearic acid, Magnesium Stearate, germicide.

In certain embodiments, the following are added ingredients (0.1 mL):—Ascorbic acid (0.034 mL), Magnesium Stearate (0.033 mL), and Stearic Acid (0.033 mL).

Mixing Schedule for 10 mL. In one bubble, mix deionized $H_2O$ with SDBS (powder) to create 5×SDBS Solution:

1. Mix 4 parts deionized $H_2O$ and 1 Part SDBS
   a. Mixing note:
      i. Volume of Powder=2×Volume of Liquid
      ii. 4 Parts $H_2O$=4 Parts $H_2O$
      iii. 1 Part SDBS (Liquid)=2 Parts SDBS (Powder)
      iv. 4 Parts $H_2O$+1 Part SDBS (Liquid)=5 Parts total volume Mix Deionized $H_2O$ with Neomycin Sulfate (powder) to create 10×NS Solution 3. Mix 9 parts deionized $H_2O$ and 1 Part NS
   a. Mixing note:
      i. 9 Parts $H_2O$=9 Parts $H_2O$
      ii. 1 Part NS (Liquid)=2 Parts NS (Powder)
      iii. 9 Parts $H_2O$+1 Part NS (Liquid)=10 Parts total volume
   a. Allows the NS powder & deionized $H_2O$ to mix
   b. Creating a 10×NS Solution In one example, mix 10×NS Solution with Versabase Cream® PCCA or equivalent thereof:

The cream that is sold under the registered trademark Versabase Cream® PCCA consists of water, ethylhexyl stearate, emulsifying wax, tocopheryl acetate, aloe barbadensis, leaf juice, disodium ethylenediaminetetraacetic acid, sorbitol, cyclopentasiloxane, methylchloroisothiazolinone and methylisothiazolinone.

4. Mix 1 mL 10×NS Solution with 5.5 mL Versabase Cream
   a. Allows the 10×NS Solution & Versabase Cream to mix
   b. Providing a milky aspect of the solution
   c. The mixture will transition to a Colloid Suspension
Mix the solutions together 5. Add 3.4 mL of the 5×SDBS Solution with the 10×NS Solution/Versabase Cream mixture
   a. Mix together
   b. The mixture will transition to a Colloid Suspension 6. Add 0.1 mL of the below Trace ingredients
   a. 0.034 mL Ascorbic acid
   b. 0.033 mL Magnesium stearate
   c. 0.033 mL Stearic acid This provides a 10 mL sample of one version of the composition of the present invention 5×SDBS Solution 3.4 mL
Versabase Cream 5.5 mL
10×NS Solution 1.0 mL
Trace ingredients 0.1 mL:
  Ascorbic acid 0.034 mL
  Magnesium stearate 0.033 mL
  Stearic acid 0.033 mL In one embodiment, the Neomycin Sulfate Solution & Versabase Cream mixing ratio is 1:5.5 weight to weight.

Another example of a formulation of the present invention includes:

| Ingredient: Neomycin Sulfate | 0.35% |
|---|---|
| Aloe Barbadensis Leaf (Aloe Vera Gel) Juice | 10.0% |
| Glycerin | 4.50% |
| Hydroxyethylcellulose | 2.70% |
| Sodium Dodecylbenzene Sulfonate | 5.00% |
| Stearic Acid | 0.30% |
| Tetrasodium EDTA | 0.20% |
| Magnesium Stearate | 0.30% |
| Ascorbic Acid | 0.10% |
| Methylisothiazolinone | 0.08% |
| Aqua (Deionized Water) | QS |

Yet another example of the present invention, includes:

| Yet another example of the present invention, includes: | | |
|---|---|---|
| Range % Inclusion | Ingredient List | One example-Amounts-gm |
| Qs to 100% | USP Purified Water | 689 |
| 0 to 10% | Glycerol | 151 |
| 0 to 2.5% | Glycerin | 37 |
| 0 to 3.6% | Polysorbate 80 | 54.5 |
| 0 to 4.1% | White Petrolatum | 62.5 |
| 0 to 0.17% | Citric Acid | 2.5 |
| 0 to 0.02% | Trisodium Citrate | 0.3 |
| 0.01 to 0.6% | Germazide Sodium dodecylbenzenesulfonates | 9. |
| 32.3% | (SDBS) of a 20% Solution | 485 |
| 0.01 to 0.03% | Ascorbic Acid | 0.5 |
| 0 to 0.03% | Magnesium Stearate | 0.5 |
| 0 to 0.03% | Stearic Acid | 0.5 |
| 0 to 0.500% | Neomycin Sulfate | 7.5 |
| 100.000% | Total: | 1,500 |

In one non-limiting example, the above formulation can be prepared as follows: Put water in tank. Add ingredients and begin mixing with high-speed prop. Add excipients until completely dispersed. Change mixing to mid-speed double motion and mix until blended. The SDBS can be at a concentration of 2 to 4%, 0.5 to 2%, 2 to 10%, 4% to 8%, 5% to 9%, 1%, 2%, 3%, 4%, 5%, 6%, 7%, 8%, 9%, or 10% weight-to-weight. When made from a 20% solution of SDBS, the final amount of the SBDS in the composition can be calculated by the skilled artisan to be the equivalent of weight-to-weight or % volume.

Yet another example of the formula is:

| Approx % Inclusion | Ingredient | Amt/Batch gm |
|---|---|---|
| 45.920% | USP Purified Water | 688.800 |
| 10.090% | Glycerol | 151.350 |
| 2.470% | Glycerin | 37.050 |
| 3.640% | Polysorbate 80 | 54.600 |
| 4.160% | White Petrolatum | 62.400 |
| 0.170% | Citric Acid | 2.550 |
| 0.020% | Trisodium Citrate | 0.300 |
| 0.600% | Germazide IIE | 9.000 |
|  | Sodium dodecylbenzenesulfonates |  |
| 32.330% | (SDBS) 20% Solution | 484.950 |
| 0.034% | Ascorbic Acid | 0.510 |
| 0.033% | Magnesium Stearate | 0.495 |
| 0.033% | Stearic Acid | 0.495 |
| 0.500% | Neomycin Sulfate | 7.500 |
| 100.0% |  | 1,500.00 |

Premix Neomycin Sulfate with Glycerin. Add to batch at room temperature. Add Ascorbic Acid, EDTA and Magnesium Sulfate one at a time. Allow minimum of 10-minutes mixing with mid-speed double-motion between each item. When batch is completely uniform, add Methylisothiazolinone. Mix until homogenous (approx. 10-minutes/100 lbs). Add Sodium Dodecyl Benzene Sulfonate (SBDS). Continue mixing at slow speed throughout filling process.

In another method for preparing the composition, add 688.8 gm of water to a 2000 ml beaker, and turn on heat. With stirring, add glycerin, Polyoxyethylene (20) sorbitan monooleate sold as" POLYSORBATE 80, white petrolatum, Mg stearate, stearic acid, SDBS and a Blend of phenoxyethanol, chlorphenesin, methylparaben and propylparaben sold as: GERMAZIDE® (or equivalent preservative) to the beaker, once dissolved slowly add glycerin mixing with a mixer, blender, or stirbar. In a separate beaker, mix citric acid, sodium citrate, and ascorbic acid to the balance of water, and mix until clear. Mix the two solutions together in a mixer and mix until smooth and lump free. Add neomycin sulfate to the vessel and mix until homogeneous. If necessary, perform reconciliation of preparation. The skilled artisan will recognize that the mixing procedure may require additional steps or changes in the order of addition of ingredients, mixing in one, two, three or more pots, stirring, dissolving, mixing, heating, cooling, changes in pH, changes in ionic strength, changes in the counter-ion or salt used, or other mechanical or physical changes to the compositions or ingredients.

One example of a stability testing specification can include:—150° F. at 10 days=1 year, with testing for an estimated minimum shelf life 30 to 36 months. In another example, the stability testing is as follows: 90 day Accelerated Micro and Compendial stability test and a real-time two year Room temperature Micro and Compendial stability test.

In some embodiments, the composition is a colloid suspension and not a true solution; the end user must shake well before using the product. In one embodiment, the composition includes a safe and effective amount of sodium dodecylbenzene sulfonate surfactant at between 1 and 10% weight-to-weight; but can also be at a concentration of 2 to 4% by weight-to-weight. In another aspect, the surfactant is in a concentration of 0.5 to 2% by weight-to-weight. In another aspect, the surfactant is in a concentration of 2 to 10% by weight-to-weight.

This embodiment of the composition was used for an in vitro susceptibility testing by agar diffusion test procedure of rapidly growing microorganisms. The composition was applied to the surface of Mueller Hinton Agar plates. Inoculated with pure cultures of clinical isolates of *Staph. aureus* and MRSA. Following incubation, the plates are examined and the zones of inhibition surrounding the drops are measured in order to determine the inhibition of the microorganisms in-vitro, as shown in FIG. 3.

Procedure. Remove the required number of inoculation tubes from box and place in test tube rack. Fill tubes with 1 ml of sterile saline. Make a saline suspension. Holding the inoculation loop perpendicular to the agar surface, select well-isolated, morphologically similar colonies. Do not penetrate the agar. Do not scrape or drag the tip across the colonies. With inoculation loop mix colonies with the 1 ml sterile saline tube. Dilute, if required, to obtain turbidity equivalent to a 0.5 McFarland Standard.

Within 15 minutes, dip sterile swab into the properly diluted bacterial suspension. To remove excess liquid, rotate the swab several times with a firm pressure on the inside wall of the tube above the fluid level.

Inoculate the entire surface of a Muller-Hinton agar plate, streaking the swab over the entire sterile agar surface. Repeat this streaking procedure two more times, rotating the plate approximately 60 degrees each time to insure an even distribution of inoculum.

Replace the tops of the plates and hold the pates at room temperature for at least 3 minutes but no longer than 15 minutes.

If the plate is satisfactorily streaked, the zones of inhibition will be uniformly circular, and there will be a uniformly confluent lawn of growth. If only isolated colonies grow, the inoculum was too light and the test should be repeated.

Dispense one free falling drip of the composition using aseptic precautions. Within 15 minutes invert the plate and place in 35 degree incubator. Examine the plates after 16 to 18 hours of incubation. Measure the diameter of zones of complete inhibition (as judged by the unaided eye), including the diameter of the drop to the nearest whole mm, using a ruler.

Field Trials were conducted to evaluate the composition as an anti-bacterial skin cleanser, which has been formulated for the following applications: 1. For an open lesion which may not be infected with bacteria, application of the present invention is intended to prevent staph bacteria, including MRSA, from forming a colony at the site of infection. 2. The composition is applied and used as directed for a MRSA-infected lesion, as the present invention is formulated to attack the bacteria, and allow the lesion to heal in a normal manner.

In certain embodiments, the composition is not a drug but a skin cleanser. It uses six mechanisms of action to attack MRSA and other bacteria. It tingles a bit when applied to an open lesion, but the sting is less than what would be felt if isopropyl alcohol were applied to the lesion.

A MRSA staph infection is a community-acquired Methicillin-Resistant *Staphylococcus aureus* (MRSA). *Staphylococcus aureus* is a common etiologic organism in soft tissue infections and may be found on the skin of nearly 20% of healthy people. Over the past several decades, infections with Methicillin resistant *Staphylococcus aureus* (MRSA) among hospitalized patients have become common. Recently, reports of MRSA infections acquired outside of the hospital setting have increased nationally.

Laboratory Test Results. The composition was tested by a physician-professional microbiologist team in an independent university pathology laboratory. Experimental culture-study results showed that a single drop of the composition completely neutralized MRSA bacteria. These results were repeated in subsequent evaluations of the composition. Laboratory culture-studies were done to evaluate the concentration-dependence of the effect of the primary active ingredient in the composition. At concentrations greater than 2%, the effect was virtually the same for all concentrations tested: a single drop of the composition completely neutralized MRSA bacteria. Laboratory culture-study evaluations of alternative products, including antibiotic products, were carried out. The composition compared favorably in these preliminary tests.

Laboratory Results: The composition was used in a laboratory setting to clean bacteria-infected lesions. Lesions that would not heal in response to antibiotic treatment showed good progress after being cleaned with the composition. A specific example of actual laboratory results involved a patient who presented with an infection that was due to a form of *Enterococcus* bacteria, based on a culture study.

A second culture test was carried out to evaluate the effects of the composition. Two specimens were taken from the lesion. The specimens were taken from the discharge (liquid) and the two specimens were taken in an identical manner. One specimen was treated with the composition; the other was not. Both specimens were sent to the lab. The lab report for the specimen not treated with the composition showed a bacteria colony count of 27 colonies. The report for the specimen treated with the composition showed a bacteria colony count of two colonies with a notation from the lab saying "scant growth."

The conclusion drawn from the culture test was that the application of the composition resulted in approximately 92.6% less bacteria. The bacteria growth from the specimen treated with the composition was only 7.4% as much as the growth from the specimen not treated with the composition.

Patient A: Fighting MRSA infection and healing lesions quickly: Patient A works in a pharmacy in Little Rock. He was diagnosed with MRSA. MRSA is a well-known staph infection that has evolved to become resistant to many forms of antibiotic treatments. The disease is systemic in nature and usually interferes with normal healing of most skin lesions. Patient A noticed inflammation around a scar from a previous MRSA-infected lesion. He used the composition on this new outbreak by applying the composition topically. He noticed some drying of the area and the skin surface flaked away after 5 to 6 days after he began using the composition. That area looked much better two weeks after using the composition and shows no signs of expanding in size or discoloration indicating continuing inflammation.

In one embodiment, the composition of the present invention is an anti-bacterial skin cleanser formulated to kill MRSA bacteria on contact. The use of the composition is intended to keep the MRSA from growing in skin lesions. MRSA bacteria cause infections and inflammation, which prevents normal healing of skin lesions. The successful application of the composition f is expected to result in the lesion to dry up. Before using the composition, the lesion is typically red and inflamed. During use of the composition, the tissue should return to a normal healthy looking pink color. Normal healing of the lesion can proceed, with decreasing Staph-Relief application over time until healing is complete.

In certain embodiment, the composition of the present invention is an anti-bacterial skin cleanser. This anti-bacterial skin cleanser was evaluated by selected individuals who suffer from systemic MRSA staph infections. In this embodiment, the composition does not treat the tissue or the body; instead, the main purpose of the composition of the present invention is to clean the lesion, killing the MRSA bacteria, thus stopping it from growing into lesions.

Patient A's next bout with MRSA-inflamed lesions followed a hunting trip. While hunting, he wore an Under Armor shirt for warmth. The Under Armor kept him warm, but the possibility of a warm skin surface, with some perspiring over an extended time is suspected to have been a contributing factor for the outbreak of lesions that followed.

This is because Staph bacteria prefer warm, damp skin areas. Bacteria do not breed and prosper well in dry lesions or on dry skin.

After the hunting trip, Patient A had approximately a dozen lesions that appeared on his skin from his hips to his armpits. These lesions showed the typical inflammation that occurs when MRSA bacteria is involved.

Patient A's physician prescribed Bactrim ointment and Bactrim oral medication, but these medications were not immediately effective in healing the new outbreak of lesions. According to the manufacturer of Bactrim, Bactrim is an antibiotic combination used to treat or prevent infections. Bactrim contains sulfamethoxazole and Trimethoprim. Side effects that may occur while taking Bactrim medication include: dizziness, headache, loss of appetite, mouth sores or swelling of the tongue, nausea or vomiting and tiredness. An embodiment of the composition, by comparison, is a skin cleanser formulated to kill bacteria on the skin with none of the side effects (given above) that are listed by the manufacturer of Bactrim.

At a certain date, the prescribed medication was continued and the composition was used on only a portion of the lesions. The lesions were observed and any difference between the ones cleaned with the composition and the other lesions not cleaned with the composition were noted.

Patient A had twelve (12) lesions ranging in size from just smaller than a dime to the size of a half dollar. He continued using the composition on three of the smaller lesions, with one application of the composition per day on the lesions. The composition was applied after a hot shower, when the lesions were wet and oozing. It was noticed that a few hours after the application of the composition, the lesions were dry and even somewhat "scaly." The composition uses gentle abrasion to achieve more-effective cleansing action. Sodium carbonate and calcium carbonate with small concentrations of silicon dioxide are used for gentle abrasion to physically remove protective films, which can harbor bacteria.

Thereafter it was noted that the three lesions cleansed with the composition improved. The spots appeared to be less inflamed, and the color begun to return to a healthy-pink color. This was particularly true for one of the troublesome lesions on his skin near the armpit. The three lesions being cleansed with the composition were healing at an increased rate when compared to the other lesions.

Based on these observations, the composition was used on all 12 of the lesions, and it was noted that all of the lesions were healing. Thereafter it was noted that the spots were drying up, and looked good. All of the lesions that previously had puss pockets were now healing, and there were no current signs of weeping or puss leakage from any of the lesions. The composition was applied two times daily for the 5 days, the drying effect was entirely adequate, and the surface of the lesions was "crusty" in appearance, which is a desired result.

Patient A sometimes feels a "needle prick" feeling when he turns or moves in a way that perhaps puts some pressure on the lesions. The cause of this occasional feeling is not known for certain, but it probably is related to a slight stretching of the thin skin as the lesions heal. His lesions seemed to be bacteria free, based on the light pink color of the healing tissue, and no sign of redness or inflammation was located, neither was swelling observed, which would normally be associated with an infected lesion.

In sum, the healing was faster after the patient started using the composition and Patient A noted that the healing definitely would have been slower without it. After the treatment, Patient A was healed, with no additional follow-up required.

Example 1

Patient B's success using an anti-bacterial skin cleanser to fight MRSA and allow rapid healing of lesions.

Patient B is an auto mechanic in Little Rock. He suspects that his first MRSA infection happened years ago, when he had a lesion under his arm, in the armpit area. Because it was slow to heal, he sought medical attention. He was treated using antibiotics and a salve for use in his nostrils. Eventually, the lesion healed at first, but he continued to have problems with infected lesions until he got a definite diagnosis, when his physician diagnosed his condition as a MRSA staph infection.

The Larger Lesion—His physician lanced one lesion, which was approximately 1 inch in diameter. It was located on his wrist.

The Smaller Lesion—When patient B showered that day, another lesion developing on the skin in the groin area was noticed. It quickly developed into a hardened knot, in the form of a circular spot about ¼ inch in diameter. The lesion was infected, as indicated by a red, inflamed appearance with a small "puss pocket" in the center of the lesion.

The Use Of the composition—Patient B began using the composition, which is an embodiment of the present invention. The formulation is described above in detail. In certain embodiments, the composition is formulated to function as an anti-bacterial skin cleanser. The composition allows normal healing of skin wounds and lesions after MRSA and other bacteria, including other staph infections have been cleansed.

Patient B left the larger lesion untreated, and used the composition on the smaller lesion. Patient B applied it three times during the course of the day and noticed that there was a mild burning sensation when the composition was applied to the open lesion. Under normal use when applied to an open lesion, the composition will cause a sensation similar to how eyes burn a bit when exposed to swimming pool water treated with chlorine. This burning feeling is usually less than the sting felt when isopropyl alcohol is applied to an open lesion.

The next day, Patient B applied the composition three times, and noticed some changes. The first change was that the knot had diminished in size. He had to "feel for the knot," because it was much less prominent than it had been on the previous day.

The second change that Patient B noticed was that the skin area seemed to be drying up.

In some embodiments, the composition is formulated to promote drying of the lesion, because staph bacteria prefer warm, damp skin areas. Bacteria do not breed and prosper well in dry lesions or on dry skin.

On the following day, Patient B applied the composition two times and continued to notice changes. The most obvious change was that the knot had diminished and it was no longer a hardened mass. The next change was that the lesion appeared less inflamed, and the discoloration of the skin had diminished. No scab had formed on the lesion during the application of the composition. He noticed that the underlying skin had begun to appear more healthy, with a "healthy pink" color, and the lesion showed slight signs of peeling.

In particular embodiments, the composition uses and abrasion compound for gentle abrasion to achieve more-effective cleansing action. Sodium carbonate and calcium carbonate with small concentrations of silicon dioxide are used for gentle abrasion to physically remove protective films, which can harbor bacteria.

On the next day, Patient B applied the composition twice and noticed a definite improvement in skin tone. The lesion was a light-pink color; the tissue color normally associated with non-inflamed, non-infected healing.

Patient B's next report was also very positive, and Patient B was very pleased with the results obtained using the composition. The lesion in the groin area (the smaller lesion) was gone. It was completely healed, with no scab or other remnants of the former lesion. The reasons that this lesion healed so rapidly were (1) the composition was used in the very early stage before the lesion developed into a larger infection; (2) this lesion was the smaller of the two lesions; and (3) the smaller lesion had not been surgically treated, so it had less trauma history.

The larger lesion, on his wrist, was much improved and healing rapidly. The tissue was a healthy-looking pink color where the puss pocket had been. The depression, presumably due to the surgery to lance the infected lesion, was healing and looked good. When asked for his opinion about whether the composition had been helpful, Patient B replied, "I believe it works!" Referring to the effect of the composition on the MRSA infected lesions, he said, "It stopped it."

After the treatment, Patient B was healed, with no additional follow-up required. This was a successful outcome, but when MRSA is in the body, it can be systemic. When this is the case, there presently is no cure. Antibiotics usually do not end the problem for life. In this case, there usually are future episodes of skin lesions that can become inflamed because of bacterial infection. When this happens, it is a good idea to begin using the composition at the very first sign of an inflamed area on the skin, so that bacteria can be prevented from forming a colony and developing into a fully developed boil.

Patient C and her bouts with MRSA and pressure sores:

Patient C is a retired schoolteacher living in Oklahoma. She was diagnosed with MRSA. She had been treated for lesions by her physicians using antibiotics and hyperbaric oxygen treatments. She experienced healing of the lesions during the months that followed.

Another lesion appeared, this lesion was most likely a pressure sore caused by physical inactivity. She was seen by her physician because this lesion presented another opportunity for MRSA bacterial infection, she was treated with Minocycline (100 mg) oral antibiotic medication. She also was treated with Clobetasol propionate (0.05%) topical ointment. Other medications, including Silvasorb, Laprox and zinc oxide treatments were used as well. Minocycline is a member of the tetracycline family of antibiotics. It has a broader spectrum than the other members of that family of antibiotics. It has been used to treat certain strains of MRSA infection. One of the great advantages of Minocycline is the inability of bacteria to become resistant to it when used to combat existing highly resistant bacteria including MRSA.

Several types of antibiotic medications, including tetracycline's, work by inhibiting the action of certain enzymes. Bacteria use to these building-block enzymes to produce proteins from which new bacteria DNA is formed. When these building blocks have been removed, the reproduction of bacteria is prevented. Over time, the existing bacteria will die but new cells will not be able to take their place and the bacterial population will dwindle. It is likely, therefore, that Minocycline also inhibits the action of other enzymes that have nothing to do with the reproduction of bacteria. This could explain why the drug is being used (in effect as an immunosuppressant) to treat multiple sclerosis (MS). A number of patients who had taken Minocycline appeared to be suffering from a form of depression or Chronic Fatigue Syndrome. Minocycline is known to cause a Serum-Sickness-Like Reaction. This is a type of delayed allergic reaction, in which the immune system interprets the antibiotic as a foreign threat, as if it were animal protein.

As noted above, Patient C also was treated with Clobetasol propionate (0.05%) topical ointment. Clobetasol propionate comes in ointment and emollient cream presentations. A very high potency topical corticosteroid should not be used with occlusive dressings. It is recommended that treatment should be limited to two consecutive weeks and therapy should be discontinued when adequate results have been achieved. Possible side effects of Clobetasol include Acne form eruptions, Allergic contact dermatitis, Burning sensations, Cracking and fissuring of the skin, Cushing's syndrome, Dryness, Erythema, Folliculitis, Hypertrichosis, Hypopigmentation, Itching, Irritation, Malaria, Numbness of fingers, Perioral dermatitis, Pruritus, Secondary infections, Skin atrophy, Skin maceration, Stinging, Striae and Telangiectasia.

Patient C is a long-term multiple sclerosis (MS) patient. She was diagnosed with MS in 1987. Because of the progression of MS, she is not physically active. The lesion, located on skin surface on the buttock, has received limited exposure to air because of her spending much time in a sitting position. The slightly inflamed area measured approximately 5 inches×6 inches, with an open lesion approximately ¼ inch in diameter.

Patient C had access to the composition near the end of her hyperbaric oxygen medical treatments but she only used the composition twice during one day and noticed some drying of the skin near the lesion. The composition promoted some drying of the lesion to discourage bacterial colony formation. Patient C did not realize that this was a desired effect, so she discontinued using the composition when she noticed the dry skin.

When another lesion appeared in the same area, Patient C decided to use the composition on a trial basis. Other than the chlorine-induced sting when applied, the composition has no known undesirable side effects. It is an anti-bacterial skin cleanser. It can be used frequently for best effect; overdose is not a problem.

After five days of application, the lesion appeared to be healing, based on a reduction of the redness and discoloration. Because of this encouraging result, she used the composition as the only topical application for the next few days as a trial evaluation. Patient C reported that the large area (4"×5") had been dark red only two days earlier, but the color had improved and the area seemed less inflamed by the following morning.

Success after only 10 days of using only the composition: From December 10 through December 20, Patient C's lesions were cleaned with the composition on a regular and frequent basis. The lesions seemed to heal in a healthy manner.

Dismissed by her physician: She saw her Physician, and during the medical examination, she was told that the skin "looks fine" and "nothing else needs treatment at this time." She was dismissed by her physician and asked to return if needed in the future. She was pleased that she was not required to repeat IV antibiotics and hyperbaric oxygen treatments for months. Her bottom-line reaction was "Hooray!"

Then another lesion developed: On Christmas day, Patient C traveled to visit friends and relatives. She was sitting either in the car or in a wheelchair for approximately 8 hours. This caused considerable stress on the skin area previously troubled by pressure spot lesions. The result was that another lesion appeared at the end of the day.

The composition was immediately used to clean the lesion. On the first day, she reported tingling when the composition was applied. Then, on the second day, less tingling was noted, followed by the third day when no tingling was noted. Her sister reported that the healing of the lesion had progressed rapidly, and was on the way to being back to normal.

Patient C and his experience using the composition: Patient D is an auto mechanic in Little Rock, Ark. Although he has not been medically diagnosed as a MRSA patient, he did develop an inflamed lesion. The lesion was on his arm, and formed a knot about the size of a half dollar. The lesion was inflamed (reddish color) and it was weeping with the production of a transparent fluid. He was given the composition, and began using it soon after the lesion developed.

Thereafter, Patient D reported that the "red was mostly gone." The size of the lesion had decreased to the size of a quarter, and the mass associated with the knot had decreased in size. He was sure that it was improving and healing. A successful result: He reported that the swelling had been considerably reduced, and the lesion had decreased in size to about ¼ inch in diameter. The lesion still showed some signs of drainage of both a transparent and a slightly yellow color. Patient D considered this lesion to be healing at a good rate.

Patient D had not taken antibiotics, so the healing is believed to be due to the body's natural tendency to heal and in this case, the healing is assisted by the composition to attack the bacterial infection. Although undiagnosed, his lesions are suspected to be MRSA, because his coworker has been diagnosed as a MRSA patient. Patient D and JW work closely together, offering the possibility of transfer of the MRSA bacteria from one person to another. When MRSA is in the body, it can be systemic. When this is the case, there presently is no cure. Antibiotics usually do not "end the problem for life." In this case, there usually are future episodes of skin lesions that can become inflamed because of bacterial infection. When this happens, it is a good idea to begin using the composition at the very first sign of an inflamed area on the skin, so that bacteria can be prevented from forming a colony and developing into a fully developed boil.

When Patient D had noticed some smaller spots on his legs, he began cleaning those spots with the composition at the very first sign of a skin lesion, so that bacteria can be prevented from forming a colony and causing a fully developed boil. Thereafter, Patient D's lesions had healed and he reported a successful outcome.

The composition was used to successfully cleanse boils: Patient E works and resides in Little Rock, Ark. Patient E works in close proximity to a co-worker who was diagnosed with MRSA that had manifested as a skin lesion. Patient E has not been diagnosed with MRSA, but she developed the signs and symptoms that she recognized from having seen the bacterial infection on the arm of her co-worker. A lesion appeared at the junction of her buttock and her groin.

When Patient E's lesion first became prominent, it started out as a knot. It grew in size and developed into a full-fledged boil. Since Anita's friend had used the composition to successfully help with the healing, she began applying the composition to the affected area. The lesion became larger and the skin broke open. The lesion was about the size of a silver dollar. Patient E applied the composition three (3) times each day. By the second day, the soreness had subsided and the size of the lesion was noticeably smaller. Cleansing with the composition was successful in allowing normal healing of this lesion.

A separate boil appeared next to the first lesion. Patient E applied the composition when she first noticed this second lesion. She continued application for three days and was continuing the use of the composition when interviewed Patient E said, "I am a true believer in the composition."

The composition was successful with Patient F, who lives in Little Rock. Patient F developed a lesion that soon developed into the same kind of lesion that she had seen on her boyfriend. She strongly suspected that she had a MRSA bacterial infection. Her lesion was on the back of her leg, at the juncture of the buttock and the thigh. The lesion began as a small red area approximately ¼ inch in diameter. It developed over a period of two days and opened to reveal a clear discharge, which was followed by a white discharge. At the point of maximum inflammation, the lesion reached the size of a half dollar and was very red and inflamed looking near the center of the lesion where the opening had developed.

The lesion developed into a knot; a hard-tissue area under the opening. The white discharge had a distinctive and strong odor that she considered very offensive. Because of the copious discharge, she kept the lesion covered and changed the bandage frequently. Because of the discomfort when sitting, she had difficulty driving for a period of 3 to 4 days.

She began using the composition at 4-hour intervals and began to notice the first signs of healing within a day. On day-2 and day-3 of the composition's applications, she noticed minor peeling of the skin at the lesion site. At this stage, she noticed definite signs of early stage healing of the lesion based on the change in color of the lesion and surrounding skin.

On day-5, the discharge had ceased and the lesion began to lose some of the red color associated with the inflammation.

On day-6 of the applications, the lesion was noticeably smaller, and the skin color had faded to a more healthy-looking pink. The signs of inflammation were very much reduced. The discharge had ceased by this time. Following day-6, she no longer needed to cover the area with a bandage. "After day-6, I didn't use the patch anymore," she said.

Then, Patient F reported that the skin on and around the lesion were "back to skin color" and the lesion had completely "healed over." The healing had progressed to the stage where she no longer felt any tingling caused by the application of the composition. Patient F believes the composition "was definitely what I needed." When asked whether she would use it again if needed she replied, "If you never had one of these sores you do not understand what it is like. I don't care how much it costs, I'd buy it."

The composition was successful for Patient G, a diagnosed MRSA patient, is a 48-year-old resident of San Diego County, California. He has skin that is sensitive, with a history of reactions to poison ivy, bee stings and what was suspected to be spider bites. Several months before this report, he had a suspected bite or sting on his left arm that developed into two infected lesions, side by side. He was seen in the local emergency room, and treated for a staph infection with necrosis (dying tissue). The attending physician's opinion was that the staph infection could have been carried by whatever bit or stung him. A culture was taken, but Patient G never learned if the diagnosis was confirmed, or if the staph was of the MRSA type.

After cleaning, the two wounds left a quarter sized holes in his arm, below a smaller opening at the surface. After treatment, the holes in his arm healed normally, without scarring.

When Patient G received two bee stings on his right hand, he developed lesions; this time more confined to the skin surface, however, spreading. He counted more than a dozen lesions located at various points on his body including his hand, wrist, arm, nose and even one on the bottom of one foot, he sought medical attention, and was treated with two antibiotics.

Cultures were taken for evaluation. Patient G was diagnosed with MRSA bacterial infections. He received the composition on Day 0. This was provided to him as part of a national field test, to evaluate the effectiveness of the composition when used to attack MRSA bacteria that prevent natural healing of skin lesions. He used the composition on some lesions and not on others. He reported a difference that was favorable for the lesions receiving applications of the composition. For example, he had one lesion that started as a small infection on the nose. He used only the composition on that lesion and experienced rapid healing which left no scars or other visible after-effects. This lesion was invisible to the physician on his follow-up visit, 2 days after applying the composition to the wound.

Patient G noticed that the healing was smoother and less crusty for the spots that were cleaned with the composition. The appearance of the other lesions did not heal as fast, or look as smooth during the same time frame," he said. After the other lesions had mostly healed, he began using the composition on his largest lesions, a spot on his wrist that had crusted over many times but did not heal like the others. "Because it was large, I applied 4 drops of" the composition, he said. "Two days later, the crust was gone, and the area became a nice pink color like the others," he said.

Thereafter, Patient G reported a successful outcome: "All of the spots are healing nicely or have already healed. All of the spots have lost their red color and have returned to a nice pink color," he said. When asked if, in his opinion, the composition had benefited him, he said, "It definitely helped."

Physician's report of successful use of the composition: the Physician used the composition to clean the skin lesion on his patient, Patient H in Russellville, Ark. Patient H, 72 years old male with a history of bacterial infection problems. Skin injury tends to be a recurring problem because he is a diabetic with a compromised healing ability. Patient H was dismissed from the hospital with a bacterial infection that was not healing. The lesion was the size of a half dollar, and it showed signs of tissue loss from the bacterial infection. The discharge from the lesion was a thick yellow fluid (pus). The lesion, including the surrounding area, was inflamed.

The patient felt discomfort and soreness in the region near the lesion. Conventional treatments, including treatment for the bacterial infection, were being continued at home, following the patient's dismissal from the hospital. The infection was due to a form of *Enterococcus* bacteria. Lab tests and results—Patient H was examined again thereafter, and the lesion had the same characteristics that had been noted previously.

A culture test was begun to evaluate the bacteria and the effects of the composition of the present invention. Two specimens were taken from the lesion. The specimens were taken from the discharge (liquid) and the two specimens were taken in an identical manner. One specimen was treated with the composition; the other was not. Both specimens were sent to the lab. The lab report for the specimen not treated with the composition showed a bacteria colony count of 27 colonies. The report for the specimen treated with the composition showed a bacteria colony count of two colonies with a notation from the lab saying "scant growth."

The conclusion drawn from the culture test was that the application of the composition resulted in approximately 92.6% less bacteria. The bacteria growth from the specimen treated with the composition was only 7.4% as much as the growth from the specimen not treated with the composition.

The turn-around—Because conventional treatments were not successful, Patient H's physician decided to treat the infected lesion with the composition. The lesion was on Patient H's back, between his shoulders. Because of the difficulty in reaching the lesion, Patient H relied on a caregiver to apply the composition directly to the infected area 5 times daily. The patient was seen again the next day and the lesion had improved. The discharge had ceased, and the opening had begun to heal. The opening was shrinking in size and had reached a smaller diameter. The opening was approximately the size of a pencil eraser.

One day later, Patient H was seen again in the Physician's office. The opening showed no drainage, and the wound was judged to be healing with good progress.

The next day, the Physician noticed that the wound opening showed continued healing with a granulated texture. The patient reported that the soreness had gone away. When speaking about the case, the Physician characterized the lesion as having shown a "vast improvement" during the three days that the composition had been applied.

Erythema is the term used to describe redness of the skin caused by dilatation and congestion of the capillaries, often a sign of inflammation or infection.

Figure 1B:
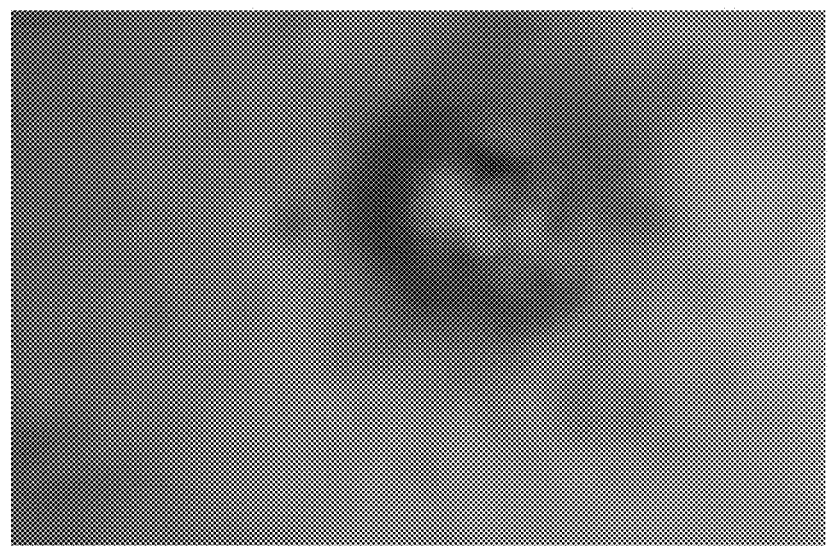

Initial Moment of treatment was started—Day 1, 48 hours after starting the composition treatment. FIG. 1 shows photographs of Patient H, which were taken by the physician for documenting the progress of the treatment using a cosmetic embodiment of the present invention. FIG. 1*a*, skin area at day 1: the area that is draining is 3 cm in diameter and the area of the Erythema was 4.5 cm in diameter. FIG. 1*b* shows the edges of the wound healing well and the over-all appearance of the wound is much improved.

Later, the physician saw the patient again. The healing process had shown very good progress. The physician said, when referring to the patient, "He was so excited. He had been using a mirror to apply the composition himself. The wound had a small scab over it and was completely healed."

Physician's second report of successful use of the composition: The physician used the composition to treat his daughter. She had developed blisters on her feet from skating, and one of the blisters became inflamed. The inflammation was a bacterial infection.

The physician used the composition to clean the lesion and the area around the inflamed area. The inflammation was quickly stopped, and the lesion healed in a normal manner with no further signs of bacterial or other infection. After treatment, the physician reported, "My daughter's wound has totally healed."

Patient I, age 65, is a retired biology teacher who has studied skin lesions, including her own difficult-to-heal lesions. She developed a wart-like growth in front of her left ear, in the hairline. The growth was removed, and when the bandage was removed, she noticed that the surgical site was inflamed. Soon, probably because of hand-to-skin contacts, she developed several lesions on different parts of her body.

More lesions—She had lesions on her shoulder, on her chest, stomach and the back of her legs. She noted tunneling (a hole in the center of the lesion), which is characteristic of staph infections. She saw her hometown physician, and she returned to her home cite and was seen in the emergency room for treatment of the lesions. She was treated with a range of medications, including antibiotics. She treated the lesions with Polysporin, Bactroban, Sulfa drugs and other medications that were prescribed for her lesions. She had only limited success, with some lesions healing slowly and other lesions developing and remaining as open sores. Patient I was not aware of any culture tests that could have been done to provide a definitive diagnosis for the kind of bacterial infection causing her skin lesions. Methicillin-Resistant *Staphylococcus aureus* (MRSA) was the suspected cause, but no firm diagnosis was given to Betty. For more than two months, she wore turtleneck tops and clothing that concealed most of the open lesions. "I have not hugged my kids and grandkids since before Thanksgiving; more than two months," she said. "This is depressing, and only adds to the other problems in my life including the loss of my husband and other family during the past four years," she said.

Patient I was enrolled in field trials approximately 2½ months after her skin lesions had begun. She was given the composition with the recommendation to use this skin cleanser every four hours for a few days until she could determine whether it was helpful in allowing the body to heal in a normal manner.

Patient I reported that her lesions were better, but she was not sure if the composition or the POLYSPORIN® had been responsible. By this time, she had used all the composition and was using only the POLYSPORIN®. She commented that using the composition every four hours was difficult because each application required approximately half an hour. She was offered more the composition but she felt that she was getting better and did need anything else for the time being.

Patient J, age 10, had multiple lesions with MRSA infection H lives in Arkansas with her mother and her father. The mother owns a business, a loan closing service, and she is a member of NNA with Certification. She suspended her professional work, to provide full-time care for Patient J. Patient J was enrolled in the composition field test.

Patient J was confined to a wheelchair, was on oxygen, and had recently lost weight rapidly, from 96 pounds to a current weight of 57 pounds. (Normal weight for a 10-year-old child is in the range of 65 to 70 pounds). She is fortunate to be receiving excellent in-home care because her mother is a registered medical assistant. Patient J was enrolled in a national field test of the composition because of multiple skin lesions, including the large bacteria-infected lesion described in more detail below.

Medical history—Prior to using the composition, Patient J had been treated with SILVIA GEL®, LANTISEPTIC®, BACTROBAN® AND ACCUZYME®. Wound #1 was being cleaned and dressed daily. Her physician described wound #1 as a pressure wound of the type often seen in nursing homes. Because of her allergies, Patient J was not being treated with antibiotics during the time she used the composition. She is allergic to penicillin and most other antibiotics.

One aspect of this case is that Patient J offers the rare opportunity to evaluate the effectiveness of the composition in the absence of antibiotic treatment. Because of this, any improvement can be attributed to the use of the composition, and not a combination of the composition and antibiotic treatment.

MRSA-infected lesions—Patient J had three skin lesions, all the result of Staph infection. The first lesion appeared in min-December, about one week before Christmas. The lesion was located on the back of the leg in the region of the buttock on the right side; a common location for so-called "pressure sores" that result from sitting long periods in one position. The lesion grew and became an open lesion. By February 14, the lesion had opened and showed signs of infection from the skin surface down to the bone. It was being dressed and treated with a Wound-Vac application. The lesion covered a skin surface area of approximately 4"×4.5" and was producing discharge as part of the indications of inflammation.

The second lesion appeared on the back of the right leg near the junction of the buttock and the thigh. By February 14, it was showing signs of inflammation, including redness, but it had not yet developed into an open lesion.

The third lesion appeared on the inside of Patient J's thigh, at the junction of the right leg and the groin. On February 14, this lesion was the size of a pencil eraser and showed signs of inflammation.

On February 14, Patient J's mother assessed the situation as critical. The largest lesion had not responded to medical treatment and all three lesions seemed to be getting worse. Her physician had given a prognosis that was not encouraging. Last resort treatments were being considered and planned, including the use of maggots to consume the dead tissue caused by the Staph bacteria.

Extensive conference-call discussions were held with the mother and those involved with the composition, and the mutually agreed plan of action was the following:

1. Patient J volunteered to establish and report photographs of the progression of the appearance of the lesions.

2. Treatment with the composition was planned for use at 4-hour intervals on all three-skin lesions.

3. Because of Patient J's unusual allergy history, a test patch on healthy skin was planned so that any possible allergic reaction to the composition could be quickly detected.

The composition has no known side effects, but people with unusual allergies can be allergic to anything, including cosmetics, lotions, and soaps that normally have no effect on most people. Because of this, a proactive "allergy watch" approach was planned to ensure that continued use of the composition could be beneficial without resulting in any unexpected allergic skin reaction.

4. The manufacturer provided cell phone contact information to Patient J's mother for 24/7 use in the event that any discussion was desired by the family. Local telephone contact information was provided so that Patient J's family could contact us, if desired.

5. The family planned continued medical attention through the wound care center, where Patient J had been receiving care prior to the time when the composition was first used to clean Patient J's lesions.

On February 16, the mother was contacted as a follow-up to the first use of the composition for Patient J. She had some good news to report. One of the lesions was an open lesion when the composition was first used on February 14. She reported that the lesion was now closed, after only 48 hours of use.

On February 19, Patient J's mother reported good results. The first lesion showed good improvement. Before the application of the composition began, the lesion covered a skin surface area of approximately 4"×4.5" and was open "to the bone." After 5 days of the composition application, the lesion was showing regranulation, the process of healing. Also, of major significance was the observation that there was almost no redness and no appearance of inflammation of the skin around the edge of the lesion. The lesion appeared to be progressing rapidly toward healing and regrowth of tissue.

The second lesion was located on the back of the right leg. By February 19, it was showing no signs of inflammation and no redness. The skin had returned to a smooth surface, and appeared to be normal, with a slightly white color. In summary, after 5 days of application of the composition, the lesion appeared to have returned to normal.

The third lesion was located on the inside of Patient J's thigh, at the junction of the right leg and the groin. Before use of the composition, this lesion was the size of a pencil eraser and showed signs of inflammation. By February 19, this lesion showed no signs of moisture or discharge; the skin had returned to a smooth texture; and the color was a healthy pink.

Her nurse visited Patient J on Monday, February 19. When observing the skin lesions, the nurse said, "This is SO much improved since I saw it last week!" On February 19, Patient J's mother wrote, "I want to truly THANK YOU for allowing us to be a part of this adventure. It has been such a blessing to us as a family. I am most thankful for the product. The product is all you claimed it would be and I feel blessed that it helped Patient J in such a time of need."

It was determined that this lesion was being affected by conditions that went beyond a Staph infection. The diagnosis received was Osteomyelitis, a condition characterized by a bacterial infection in the bone. The lesion was being treated with a wound Vac that was being changed three times each week. At 8-hour intervals, she was being given IV antibiotics of two kinds—Vancomycin and Merrem IVs.

The composition was also being used on this most difficult of lesions, and there was some good news. The lesion had begun to granulate (healing progress).

In closing this field test report, the use of the composition can be summarized as follows: The use the composition on the first lesion was helpful, but did not result in rapid healing. This lesion was affected by conditions that went beyond a Staph infection of a skin lesion. Before the composition was used, the infection had progressed deep into the tissue, to the bone. The diagnosis was Osteomyelitis.

Osteomyelitis is an acute or chronic bone infection, usually caused by bacteria. The infection that causes Osteomyelitis often is in another part of the body and spreads to the bone via the blood. In children, the long bones are usually affected. Bone infection can be caused by bacteria or by fungus. When the bone is infected, pus is produced within the bone, which may result in an abscess. The abscess then deprives the bone of its blood supply. Chronic Osteomyelitis results when bone tissue dies because of the lost blood supply. Chronic infection can persist intermittently for years.

The lesion was being treated with IV antibiotics of two kinds—Vancomycin and Merrem. Merrem/Meronem (Meropenem) is an ultra-broad spectrum injectable antibiotic for a wide variety of serious infections, including meningitis and pneumonia.

The composition was also being used on this most difficult of lesions, and there was some good news on March 25. The lesion had begun to granulate (healing progress) following an extended and complex medical treatment.

The use of the composition marked the turn-around and the progression of healing for the second lesion. Continued use of the composition resulted in the skin area being able to heal naturally and rapidly.

Patient J's pediatrician took special note of the total healing that had occurred with the second lesion and the third lesion (described earlier). He asked Patient J's mother about the history of those lesions and the causes for the rapid and complete healing that had occurred. Patient J explained, "those lesions healed because of the use of [the composition], a product that is not yet on the market, which is why he was not familiar with it." After a thorough physical examination of the healed skin, the physician said, "whatever it is, it did a good job."

Patient K reported that the composition for acne. She said that for several years she had sties on my eyelids. Most sties fill up with a liquid type substance similar to a blister, where you can lance them and they will go away. Mine are the type that fill up with a "cheese like" consistency and must be cut out by an eye doctor. My doctors have given me everything from topical ointments to antibiotics to try to prevent them from reoccurring. The doctor has stated it might be caused by a viral infection.

Patient K reported that when stress level went up, they seem to appear more often stating the following: I can usually tell when they are going to appear, as the lid will start itching and cause discomfort I started using the composition for acne on the eyelid with a Q-tip. I put a drop on a sterile Q-tip and apply to the eyelid. It sooths the itching immediately and it has stopped the sties from forming. I am very impressed with your product. As I stated before . . . I've tried everything and nothing seemed to work until I tried your [the composition] for acne. It is wonderful!

Patient L: 5-day recovery from MRSA reported by Patient L, who is a schoolteacher. Her husband was diagnosed with Staph infection. Her pharmacist recommended that her husband use the composition on the skin lesion. The lesion had developed to the stage of a boil, and his physician had lanced it as part of the medical treatment for the Staph infection.

Five-day recovery—the composition was frequently applied to the lesion, beginning after the lesion had been lanced. After only five days following the surgical procedure (and after five days of use), the patient was seen by the surgeon as part of a follow-up medical appointment. According to Patient K, the surgeon "was amazed that it looks as good as it does." The physician made favorable comments about the results and about the composition, saying, "it was probably some good stuff."

Patient L reported some comparison information. "I compared the recovery time with someone else that had the same Staph-infection condition that my husband has. He said that it would take a good 2½ to 3 weeks to recover."

Patient L stated, "I am convinced that this wash did help the healing process. Even though the staph infection is not totally gone yet, it is well on its way. I personally have not ever had Staph infection, but I watched my husband suffer and I know that this is something that I never ever want to have. I am thankful for the samples that I received for my husband and I think that if you have Staph infection, you will want [the composition]. It will cut down on the time that you have a staph infection."

Following the successful recovery, there was some question about which kind of bacterial infection might have been the cause of the problems, based on the physician's opinion. Even with this degree of uncertainty, the physician made favorable comments about the results and about the composition, saying, "it was probably some good stuff"

Los Angeles man, wife and daughter acquired MRSA and used the composition Patient M works for a film company in Los Angeles. His Staph infection began with a scrape on his hand that rapidly developed into an infection. His physician diagnosed the infection as a MRSA bacterial infection based on a culture test. Patient M's wife also tested positive for MRSA based on the results of a nasal culture, but did not develop bacterial infections (skin lesions) as of the time Patient M was enrolled in our national field test to evaluate the composition.

Patient M's daughter is 5 years old. She developed MRSA that began with a skin lesion on the nose. She was being treated with sulfa drugs at the time the family was enrolled in the field test.

The skin lesion on his hand was followed by another lesion on his back near the waistband. The lesion on the back grew to the size of a golf ball. Patient M was treated with Kevlex, Bactrim and surgery before requesting the composition.

Figure 2A:
FIGS. 2a and 2b show the progress of treatment.
Figure 2B:
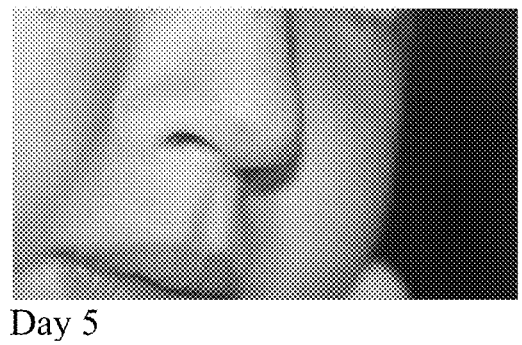

The composition product was used to treat Patient M' daughter's lesion on her nose. The following photos show the progression from Day 1 through Day 5 of treatment with the composition, shown in FIG. 2, at day 1 and day 2.

Patient M's report was, "Here are three photos of my 5½ year old daughter [ . . . ]. Day one was the day we received [the composition] and day 5 was after three applications." "It was very successful. These photos are in order of use on the small occurrence on her nose." "Thank you so much, we have had no recurrences so far."

Patient M used the composition to obtain success after receiving conventional medical treatment. Patient M develops contracts for racetracks and travels extensively as part of her work. Her experience with a Staph infection has been a long, painful experience that has at last seen a turn-around and improvement resulting from the use of the composition.

She had knee surgery at a hospital and subsequently developed a lesion in her nose. She has been under the care of eight physicians in her attempts to seek treatment to stop the loss of tissue that resulted from the continuing expansion of the lesion. Her description of the long-term result is that the inside of the left nostril was almost destroyed.

She was diagnosed with a Staph infection in her nose. The lesion was inside the nasal cavity and did not respond to conventional treatment.

Conventional medical treatment—Her lesion had resulted in a loss of tissue that was so extensive that reconstructive surgery, at a cost of $15,000 was being considered. Her physician could not perform the surgery until the bacterial infection could be cleared up, because surgical intervention would only provide more opportunity for the bacteria to colonize and expand. By this time, the lesion was "a raw sore" as she described it, and it often would bleed, even at night during sleep.

Results—She used the composition in two ways: First, she applied it with Q-tip. Later, she learned that if she uses a small section of surgical sponge she could put a couple of drops of the composition on the sponge and leave it in the nasal cavity when at home or when sleeping.

"Healing began quickly after I began using [the composition]," she said. When interviewed on Apr. 25, 2007, she described the improving condition of her nose as: "The bleeding has stopped; there is no more bleeding." "The healing has continued to progress since I began using [the composition]." "The healing has resulted in some re-growth of tissue; the tissue in that area is thicker than it was."

Physician's review of the composition. Field test results reported in this document, and other relevant information was reviewed by a physician having an interest in the use of the composition. The following are examples that were provided by the physician in summary format.

Example 2

Testing was conducted at a pathology laboratory certified for microbiology testing by a physician and a microbiologist. A double blind, randomized controlled experiment was conducted to evaluate the SBDS surfactant against bacteria in Petri dishes.

Bacterial strain: Two well characterized strains of methicillin-sensitive *Staphylococcus aureus* (MSSA) and methicillin-resistant *Staphylococcus aureus* (MRSA) were used. Specifically, experiments used ATCC 29213 (MSSA) and ATCC 43330 (MRSA), both beta-lactamase positive strains, which represent greater than 90% of the respective strains in the American population.

Petri dish preparation: A sterile cotton swab (American Scientific Products, McGraw Park, Ill.) was dipped into the cultures and used to swab the entire surface of 150×15 mm Petri dishes containing 75 ml of standard Mueller-Hinton agar. Two Petri dishes were inoculated with ATCC 29213 (MSSA and two Petri dishes with ATCC 43330 (MRSA). One Petri dish of each group (MSSA and MRSA) was set aside as the controls. The other two Petri dishes (MSSA and MRSA) were divided up in quadrants, and each quadrant was labeled B, C, D or E.

The composition can be prepared with a surfactant concentration of 2 to 4%, 0.5 to 2%, 2 to 10%, 4% to 8%, 5% to 9%, 1%, 2%, 3%, 4%, 5%, 6%, 7%, 8%, 9% weight-to-weight. To evaluate a wider range of surfactant concentrations, cleanser compositions were prepared as follows: A surfactant solution and a stock solution were mixed in various ratios to produce four skin cleanser solutions having four different surfactant concentrations of 0.5, 1, 2, 3, 4, 5, 6, 7, and 8%, weight-to-weight. The amount of other ingredients in each of the four skin cleanser solutions was less than 1% concentration weight-to-weight.

Cleanser Testing: Four samples of the cleanser with the four different concentrations of the surfactant (0.5, 1, 2, 3, 4, 5, 6, 7, and 8) were placed into four separate, unmarked bottles. Each bottle was randomly labeled (B, C, D, or E), and the microbiologist conducting the study was unaware of any difference between the solutions.

Application: Holding each bottle vertically, the microbiologist added a single drop from each bottle (B, C, D, or E) to the corresponding quadrant of the labeled Petri dish. All four Petri dishes were placed in an incubator overnight at 37 degrees Celsius, and examined 20 hours later. Petri dishes were compared to the corresponding controls, and zones of inhibition were characterized by the largest point of diameter of the circle or oval.

Results: The solution with the lowest surfactant concentration, 0.5%, showed no difference between the controls, while the 1% and 2% concentrations inhibited approximately 50% of the colony forming units (CFUs). The 8% concentration showed clear inhibition of the bacteria in a large circle of approximately 40 mm in diameter.

Example 3

The same protocol as described in Example 2 to test various concentrations of the surfactant compound against the MRSA strains and revealed a clear trend, with higher concentrations of the surfactant causing larger zones of inhibition [range from zero (control) to 42.3 mm (14.80% concentration)].

Table 1 shows the inhibition zone diameters shown in the table below were averaged over three repeated experiments.

| Diameter of Zone of Inhibition (mm) | Surfactant conc. (vol. %) |
| --- | --- |
| 42.3 | 14.80% |
| 41.7 | 4.90% |
| 39.3 | 4.00% |
| 39 | 6.50% |
| 37.3 | 3.30% |
| 35.3 | 2.30% |
| 34 | 9.30% |
| 33.7 | 2.50% |
| 32.7 | 2.80% |
| No Change | 1.00% |
| No Change | 0.00% |

Example 4

Four cleanser compositions were prepared and tested in the manner described in Example 2, except that each cleanser contained a different surfactant. Four control compositions containing only the surfactants were also prepared and tested in a similar manner.

All four cleansers evaluated in this example showed definite effectiveness as anti-bacterial and anti-septic agents. Each of the four surfactants proved effective when mixed with water only than in the presence of chlorine.

A 5% solution of surfactant in the stock solution (containing chlorine) was as effective as a 10% concentration of the surfactant in water (without chlorine).

Example 5

Addition of 10% dye by volume to a solution containing surfactant dramatically improved the effectiveness of the cleanser as an anti-bacterial agent. The zone of inhibition increased 66% (from 62 mm to 80 mm diameter) when 10% (by volume) ionic dye was added.

Example 6

Action against Gram-positive bacteria such as *Enterococcus*: A 68-year-old man with long history of diabetes was admitted from his hospice care home to an acute care facility hospital secondary to an infected decubitus ulcer (bedsore).

This patient's sacral ulcer tested positive from culture swab for *Enterococcus*, a common Gram-positive bacterium for infecting bedsores. Immediately upon admission, the patient was placed on antibiotics (ciprofloxacin). Over the next five days, the 4 cm open, oozing ulcer with erythematous margins and discharging pus showed signs of worsening. On day five, the treating physician directly cultured the wound again with two cotton swabs. Cotton swab #1, the control, was placed directly in the sealed container based on hospital protocol. Cotton swab #2 was placed into the sealed container, with one single vertical drop of cleanser solution with the composition of the present invention. Both swabs were sent to the lab and a count of colony-forming units (CFUs) was ordered.

Forty-eight hours later, the culture of cotton swab #1 (the control) exhibited 22 CFUs, while the culture of cotton swab #2 had only two CFUs. Moreover, the patient's ulcer showed marked improvement within 24 hours of the first application of the composition. There was sufficient resolution (decreased Erythema, lower indurations, skin color improvement from red to pink, and decrease pus discharge) of the ulcer over the next four days for the patient to leave the hospital.

Example 7

Action against Mycobacteria: A 39-year-old female with four-month long history of an infection on the posterior aspect of her right ring finger was treated. The infected areas were culture positive for mycobacteria marinum, with symptoms of infection resulting in a 4 cm long patchy zone of Erythema, indurations, and oozing from the wound. After failing two full courses of oral antibiotics, over the previous four months, the patient was given a third round of antibiotics, this time Clarythromycin, after her finger's condition had worsened. After eleven days of antibiotics and no change in symptoms, the patient applied two drops of the composition into the wound three times per day where a 5 mm biopsy had broken the skin, and applied gentle abrasion as directed. Within 24 hours of the first application, the wound showed marked improvement in the overall signs of infection. Within 72 hours, the area of the open skin lesions had a continued decrease in indurations, Erythema and signs of infection. The patient's symptoms ultimately improved with the combination of antibiotics and the composition.

Example 8

Goat and other farm animals are very susceptible to infections. Often, if a bad infection occurs, the animal will be separated and sacrificed. A goat (with an ophthalmic infection resulting in large greenish discharge from both eyes for three weeks) was treated with the composition. The cleanser was squirted into the eyes of the goat for two days. Within 24 hours, the goat's eye infections had improved, and the goat was able to see out of one of the eyes. The treatment was continued for five days resulting in the full resolution of the goat's symptoms.

Example 9

Five patients with confirmed MRSA positive infections by their doctors were treated with the composition by direct topical application on the surface of their skin and open lesions. Within 24 hours, three of the patients improved such that their areas of skin Erythema, indurations and open lesions appeared more normal. All five patients infected area showed complete resolution of his or her acute symptoms within five days of starting the treatment.

Example 10

A patient with a 12-month history of culture positive MRSA returned from a hunting trip with a dozen skin lesions on his skin from his hips to axillary region. The patient was started on oral and topical sulfamethoxazone and Trimethoprim combination antibiotics, with no change in symptoms. On day 6 of the antibiotics, patient applied the composition on the skin of three of the 12 lesions, and experienced marked improvement over the first 24 hours and by the fourth day patient's three lesions had returned to a healthy pink color. He then applied the composition to all twelve lesions, and after seven days of subsequent cleanser treatment, combined with the continuation of his antibiotic regiment, showed all the lesions dried up with a healthy fleshy skin toned appearance.

Example 11

A 35-year-old male patient was diagnosed by a physician with MRSA skin infection, with two active 1 cm and 4 cm skin lesions. The patient applied the composition on the small 1 cm lesion three times per day with concomitant application of gentle abrasion while leaving the larger lesion alone as the control. Within one day, the smaller lesion had dried and patient reported in the appearance and feel of the infection under the skin as well, reporting less inflammation. After ten days, the smaller lesion had turned a healthy flesh toned color with no scab or other remnant; in addition, complete resolution. On day five, the patient began using the cleanser on the larger lesion, and this larger lesion, which had been unchanged compared to the healing of the small lesion, showed immediate improvement after the application of the composition, with similar course of action as the smaller lesion.

Benefit: the composition contains a cleanser for use on skin that is specifically formulated to remove MRSA and staph bacteria.

Directions for use: use this product as a cleanser by gently rubbing it on skin with a clean Q-tip. Repeat process every 4 hours or as needed.

Mechanisms of action: (1) Contains a skin cleanser. (2) Contains antibiotic for bacteria control. (3) Contains an anti-bacterial surfactant to wash away dirt and oil films that can harbor bacteria. (4) Formulated to slightly dry the skin. (5) Uses gentle abrasion to achieve more effective cleansing action.

Ingredients: Deionized water, Neomycin Sulfate, Ascorbic acid, Sulfonate, Versabase Cream® PCCA, Sodium Dodecylbenzene, Magnesium Stearate, and Stearic Acid. The cream that is sold under the registered trademark Versabase Cream® PCCA consists of water, ethylhexyl stearate, emulsifying wax, tocopheryl acetate, aloe barbadensis, leaf juice, disodium ethylenediaminetetraacetic acid, sorbitol, cyclopentasiloxane, methylchloroisothiazolinone and methylisothiazolinone.

Contains no alcohol. Contains no animal products.

Caution: For external use only on skin. Keep out of reach of children. Eye irritant. Do not swallow or inhale. Ask a physician before use if you have unusual allergies to any ingredients listed above. When using this product, in the event of unexpected side effects, discontinue use, cleanse the area with water and see a physician. No harmful effects are known to result when used as recommended.

Net weight is approximately 3 gram, and net volume is approximately 3 ml.

Example 12

Patient N: age 60, was diagnosed with diabetes 5½ years before her bout with MRSA. Her struggle began when she felt a something on her abdomen while she was outside. She was wearing a loose blouse, not tucked in at the waist. The feeling may have been a spider bite, but this is speculation since no spider was seen. The area developed into an open skin lesion over the next several days and the opening continued to expand and grow deeper. After being admitted to the hospital, Patient N was seen by a board certified infectious disease specialist. He diagnosed the trauma as a MRSA infection. This diagnosis was confirmed later by the results of a culture test.

Day −3: The black region in the center of the wound is necrotic (dead) tissue, as seen in FIG. 7. The cleaning and removal (debridement) of necrotic tissue is a prerequisite for successful wound care and healing. If debridement is not done, wound repair is significantly impaired. Necrotic tissue in the wound becomes a breeding ground for bacteria and may lead to gangrene and septicemia that can result in death. A cleaning procedure was done to remove black (dead) tissue from the wound. Patient N was treated with Vancomycin, a glycopeptide antibiotic used in the treatment of infections caused by Gram-positive bacteria including MRSA. Vancomycin has traditionally been reserved as a drug of last resort however it is usually effective for only about 40% of MRSA patients. The flesh-eating bacteria continued to eat away at the tissue on her abdomen. Patient N was treated with Vancomycin and other medications, including pain medication administered via an IV, until the drugs caused her blood pressure to drop to dangerously-low levels.

Day −2: Patient N was told that the pain medication was the cause of the first indication of possible renal failure. IV-administered pain medication was suspended on Thursday, and not resumed during her stay in the hospital. Because the wound was in the fatty tissue, Patient N did not experience intense levels of pain and discomfort although the lesion was both deep and infected.

Figure 7A:
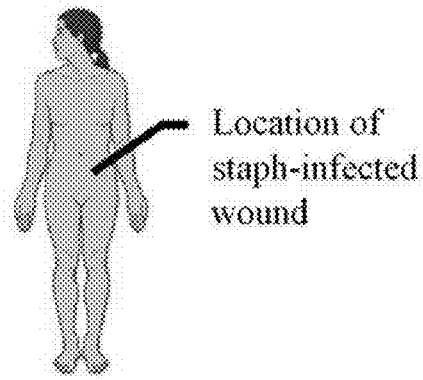
FIGS. 7a to 7f show the progress of treatment of Patient N.
Figure 7D:
Figure 7B:
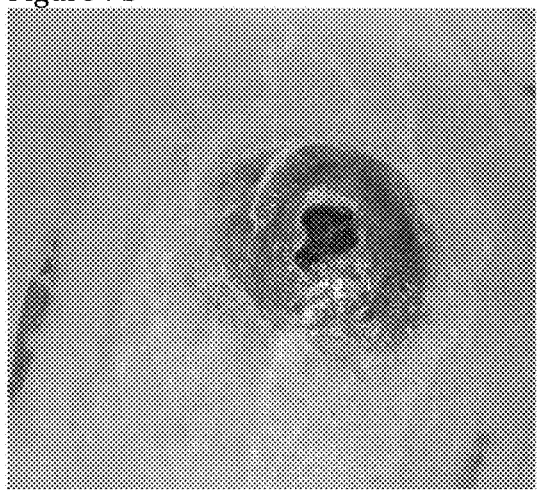
Figure 7E:
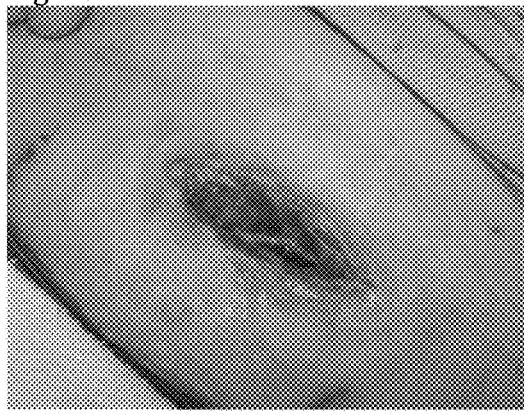
Figure 7C:
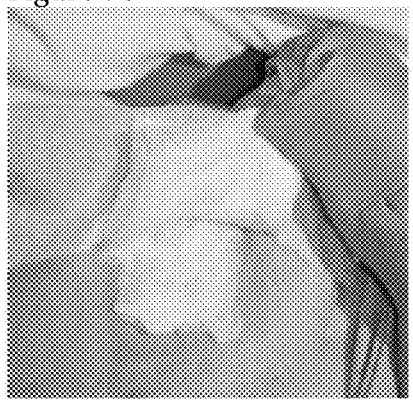
Figure 7F:

Day −1: Because of the adverse drug effects, antibiotic drug treatment was suspended on August 10, even though the lesion had grown to a width of 3 inches and a depth of 2.5 inches, as shown on the photographs below. The first photograph shows the wound dressing being removed on Friday afternoon, as seen in FIG. 7c. The photograph in FIG. 7d shows the wound as an oval opening, 3 inches long, 1 inch wide and approximately 2.5 inches deep as measured by Q-tip probes. This photo was fourteen days after the first indication of skin trauma and after the wound had become infected with MRSA.

Day 0 of use of the composition: The situation was clearly degrading and treatment options were needed. The wound showed no signs of improvement. The drug of choice had been suspended because of undesirable side effects. The situation was becoming worse, and there was danger of the bacteria eating through the abdominal wall, causing a potentially life-threatening condition. The character of the wound had taken a turn for the worse. A tunnel was detected during the examination of the wound. The tunnel extended from the primary opening toward the navel. The length of the tunnel, when probed, was ½ inch in length, indicating that the flesh-eating MRSA bacteria was advancing. The situation was clearly degrading and treatment options were needed.

Following the family's request, Patient N's physician allowed the use of the composition. There are no known side effects from the use of the composition; and there are no known interactions with drugs. The composition is not a drug, it is a bacteria-killing skin cleanser that kills staph bacteria on contact when tested in-vitro under controlled laboratory conditions. The composition had previously been used by many people as a topical application to kill staph bacteria, but Patient N's skin lesion was different. In her case, the lesion was a deep lesion, and because of that, the composition was to be used as an experimental treatment. Prior to treatment, the lesion was cultured and lab results showed that there was a "light growth of MRSA."

Note the red/purple color of much of the lesion in FIG. 1e. This tissue color indicates the presence of inflammation commonly seen at the site of bacterial infections. The photograph above shows the first application of the composition at 5 p.m. on August 11. It can be seen as the blue liquid at the bottom of the lesion. The composition was sprayed on and into the wound by a hospital nurse using a Q-tip to apply the liquid to all accessible surfaces of the lesion. Patient N was asked to quantify the degree of tingle caused by application of the composition, with a scale of 0 to 10 being defined as 10 being the measure of strong pain. She reported that the tingle was perhaps 2 to 3 on that scale, and the discomfort was entirely manageable. After the first application of the composition, the wound was packed with saline-solution-soaked gauze, and left that way for the following 12 hours.

Day 1 of use, 5 a.m.: the wound was dressed again at 5 a.m. on Sunday morning. The appearance of the wound in FIG. 7f. The dark area in the center of the wound is the blue color of the composition that was applied by the nurse when the dressing was changed. The nurse noted that healing was indicated by a granulated ridge forming on the top layer of the wound. There was no observable black tissue. There was no blood draining from the any part of the wound. She also noted the encouraging change in color of the wound during the 12 hours since the first application of the composition. As shown by a comparison of the actual photos, the color had changed from a red/purple look of inflamed tissue to a more pink color indicating much less inflammation.

Upon observing the wound and commenting on the change in characteristics during the 12 hours since the beginning of cleansing with the composition, the nurse said, "This looks very, very good. Healing is beginning" The most important observation was that the tunnel had closed, indicating the "turnaround" in the condition. "Turnaround" is defined here as a reversal in the progression of trauma followed by observable healing. The nurse was amazed that the tunnel was closed. The complete closure of the tunnel had obviously occurred as a result of healing during the past 12 hours. The lesion was probed carefully to ensure that the tunnel was indeed closed.

Patient N reported a tingling level of 2 to 3 on a scale of 0 to 10; essentially no change when compared to the sensation she felt 12 hours earlier during the first application. Note the improvement in the color of the tissue. Since the first application of the composition, the red/purple color of the tissue had begun to change to a lighter color, indicating less inflammation of the tissue.

After the application of the composition, the wound was packed with saline-solution soaked gauze, and left that way for the following 12 hours.

Day 1 of use—4:45 p.m. to 5 p.m.: A new complication, not related to the use of the composition, was noted; first stage renal failure was evident. Urine output was subnormal. A physician's assessment was that the first-stage renal failure was being caused by drugs, and prescription drug adjustments were made. At about 4:45 p.m. on August 12, Patient N was seen an infectious disease specialist at the hospital. She pulled back the dressing, observed the healing progress of the wound, and said, "this looks very good." The wound was dressed again at 5 p.m. on Sunday afternoon. The most important observation was that the depth of the wound had decreased from 2.5 inches to approximately 1.5 inches. This remarkable change was documented, but remains unexplained. Under normal conditions, healing would not proceed this rapidly. In Patient N's case, this rapid healing rate was very remarkable in view of her diabetic condition that normally would result in slower-than-average healing rates for any lesion.

Patient N reported a tingling level of 2 to 2.5 on a scale of 0 to 10; a minor improvement when compared to the sensation she felt 24 hours earlier during the first application of the composition. Because of the excellent healing that had been observed, and because no side effects had been observed due to the effects of Staph-Relief, the confidence levels of the patient, the family and the medical team had grown rapidly over a 36-hour period since the composition was first used to treat the wound. After the application of Staph-Relief, the wound was packed with a gauze soaked with the composition, and left that way for the following 12 hours. Prior to this, the wound had been cleaned with saline-solution-soaked gauze, followed by an application of the composition. The wound was then packed with saline-solution-soaked gauze. Day 2 of use, Monday, 6:30 a.m. Prescription drug adjustments to reverse the first-stage renal failure were successful. On Day 2, Patient N's urine output had resumed and renal failure was no longer a concern. Her blood pressure had stabilized allowing antibiotic treatment to resume. She began taking Vivox (oral medication), a doxycycline from the tetracycline family of antibiotics. The wound was dressed again at 5 a.m. on Monday morning. The appearance of the wound is shown in the next photograph. The dark area is not tissue; it is the blue color of the composition.

Upon observation, the nurse said, "the color looks better than it appeared yesterday." No blood seepage, no puss and no black tissue was observed. Patient N reported no tingling during the application of the composition. This corresponded to a tingling level of ZERO on a scale of 0 to 10; an extremely strong improvement when compared to the sensation she felt 36 hours earlier during the first application of the composition. "No tingling" was the most important change noted on Monday morning. This observation indicated that very significant healing had occurred. The composition causes no tingling when applied topically to healthy skin. The patient-reported reduction in tingling has consistently corresponded with increases in healing when the composition has been used to cleanse skin lesions.

Day 2 of use 5 p.m.: When the dressing was changed, the hospital nurse observed the wound and no blood seepage, no puss and no black tissue was reported to the patient. Patient N reported no tingling during the application of the composition. This corresponded to a tingling level of Zero on a scale of 0 to 10. This report is consistent with tissue healing. Rapid healing progress was obvious, and there were no signs of residual or recurrent bacterial infection.

The infectious disease specialist said that the patient was a candidate for release from the hospital.

Figure 8A:
FIGS. 8a to 8f show the progress of treatment of Patient N.
Figure 8D:
Figure 8B:

Day 3 of use: The dressing was changed in the morning and again in the afternoon. A new nursing team began caring for Patient N on Day 3. Each time the dressing was changed, the composition was used to treat the wound. FIG. 8c shows the wound in the morning. The blue color is the liquid composition in the wound.

When the dressing was changed, the hospital nurse observed the wound and no blood seepage, no puss and no black tissue was reported to the patient. Patient N reported no tingling during the application of the composition. This corresponded to a tingling level of Zero on a scale of 0 to 10. This report is consistent with tissue healing.

Rapid healing progress was obvious, and there were no signs of residual or recurrent bacterial infection. Patient N's progress was deemed good enough that hospitalization was no longer required. She was discharged from the hospital at 8 p.m., and she returned to her home.

Day 4 of use: On her first morning after returning to her home from the hospital, Patient N's husband applied the composition and observed no complications when changing the wound dressing. Patient N was feeling good and she was "up and about." She was walking from room to room and beginning to lead a normal life again. The wound care was transferred to a team of visiting home-health nurses on Wednesday with a plan for scheduled visits twice each day for the purpose of changing the dressing on the wound and observing the healing progress.

Day 6 of use: The dressing was changed in the morning and again in the afternoon. FIG. 8d shows the wound in the afternoon. This photograph can be compared with the photographs of the wound taken on Day 0 to give a comparison over a 6-day interval during which the composition was being used as a wound cleanser. A precision measurement of normalized-dimension photographs shows that the wound has decreased in length by 6.5% during the 6 day interval. The granulation and healing progress is clearly evident in the photos. The closure of the wound is clearly seen in the photograph above, as inflamed tissue turns to healthy-looking tissue at the edges of the wound during the healing progress.

On Day 6, Patient N said, "I can tell that it has healed a lot, because it takes much less gauze to pack the wound. Now, when the nurse packs the wound, it takes only about ⅓ as much gauze compared to what was required when I was in the hospital." "I know I am better. I stopped taking oral pain medication on Day 5. I was given another prescription for Vicadin, but I didn't need it."

Day 12 of use: Patient N was seen by her surgeon, and when examining the wound, he said, "Wow! That looks good!" The wound had healed from a 2.5 inch-deep wound to a ¼ inch-deep wound in only 12 days.

Day 17 of use: Patient N was interviewed to learn her feelings about her progress. She was living a normal life—cooking for her husband and three grandchildren. She had been driving since returning home from the hospital. Her husband continued dressing the wound, but only once per day because of the degree of healing. She reported the "tingling and stretching" that often occurs during healing of the skin. She reported that the lesion had begun to heal and close from the ends toward the center. Her husband noted a very small amount of blood during the changing of the dressing, but noted that healing progress was being observed on a day-by-day basis. The lesion maintained a ¼ inch depth as the healing progress continued from the sides and skin surface of the wound.

Figure 8E:
Figure 8C:
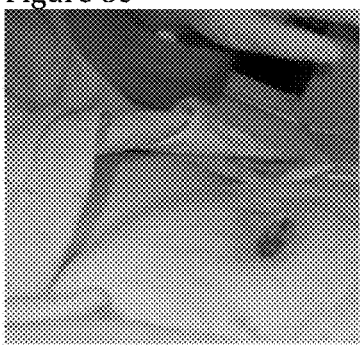
Figure 8F:
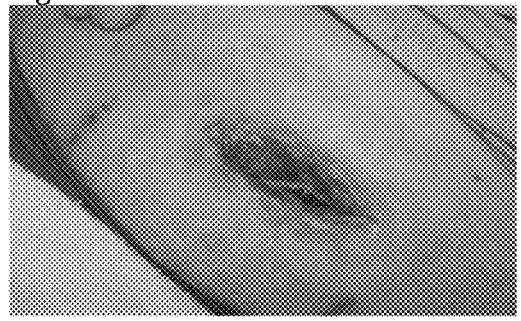
Figure 9A:
FIGS. 9a to 9f show the progress of treatment of Patient N.
Figure 9D:
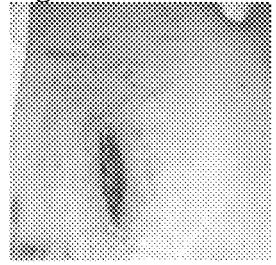
Figure 9B:
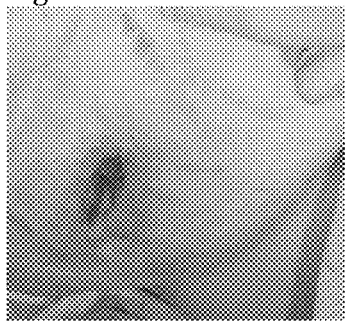
Figure 9E:
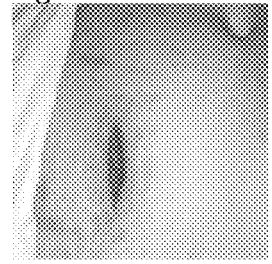
Figure 9C:
Figure 9F:
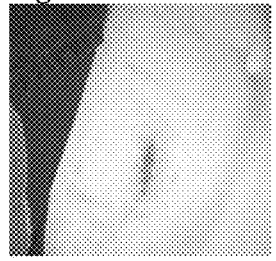

Photograph time sequence showing healing progress are shown in FIGS. 8e and 8f; on August 10, before cleansing began and August 11, the day cleansing began (right).

Example 13

Figure 4A:
FIGS. 4a to 4f show the progress of treatment of Patient O.

Patient O: The lesion on Patient O's arm was first noticed on Day 0. FIG. 4a shows the lesion on Day 7, only one week after the lesion was first noticed. This photo was taken before treatment with the composition began. The depth of the lesion was about ½ inch at that time. Staph MRSA is a flesh-eating bacteria which consumes tissue, kills the tissue, and tunnels deeper with the passage of time. FIG. 4b shows the wound 8 hours after first application of the composition.

Application of the composition began on Day 8. The photo (FIG. 4b) was taken 8 hours after the first application of Staph-Relief and documents initial improvement in the color of the tissue, indicating a reduction of inflammation.

Figure 4D:
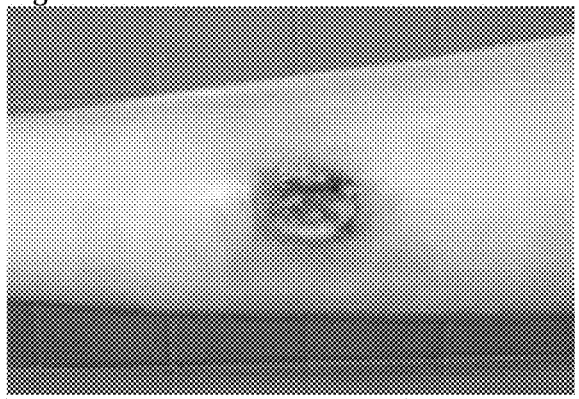
Figure 4B:
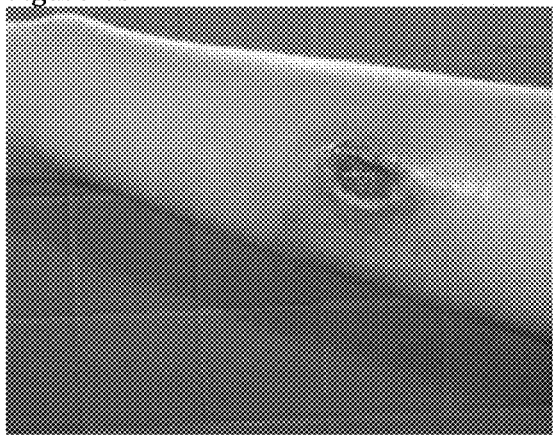
Figure 4E:
Figure 4C:
Figure 4F:
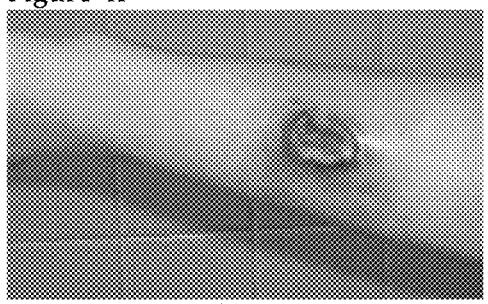

Improvement after 12 hours after first application of the composition is shown in FIG. 4c. The wound looked more like a wound than an infected sore now. The improvement was remarkable.

Improvement after 22 hours after first application of the composition is shown in FIG. 4d. The wound began healing, there are no signs of puss, and the swelling has diminished.

Further improvement after 24 hours after first application of the composition is shown in FIG. 4e. The wound began healing, there are no signs of puss, and the swelling has diminished. The bacteria can regenerate within 6 hrs; therefore in a preferred embodiment, the dressings is changed at least every 5 hrs.

Figure 5A:
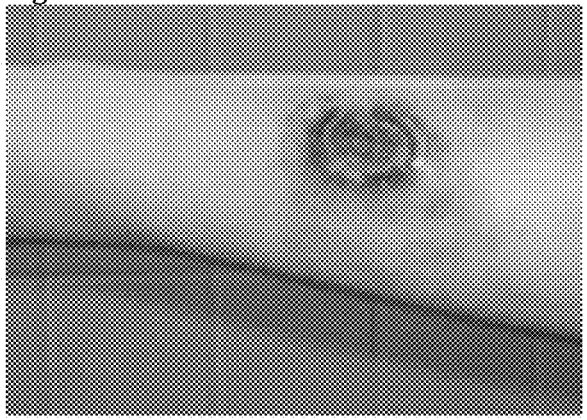
FIGS. 5a to 5f show the progress of treatment.
Figure 5B:
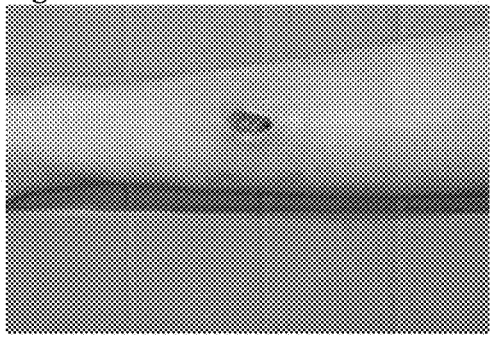
Figure 5C:
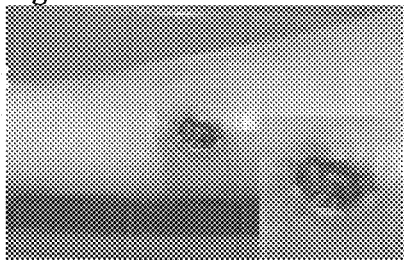
Figure 5D:
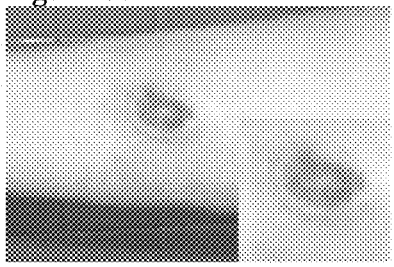
Figure 5E:
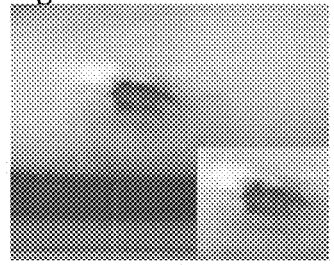
Figure 5F:
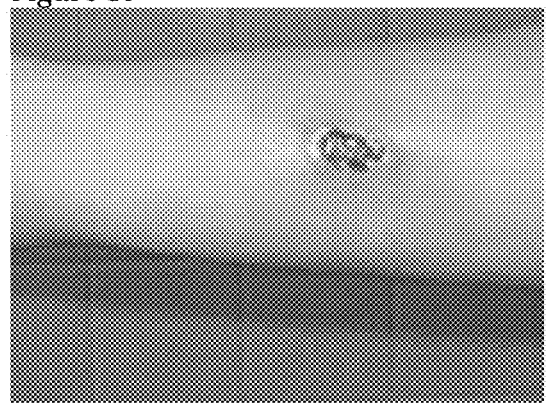
Figure 6A:
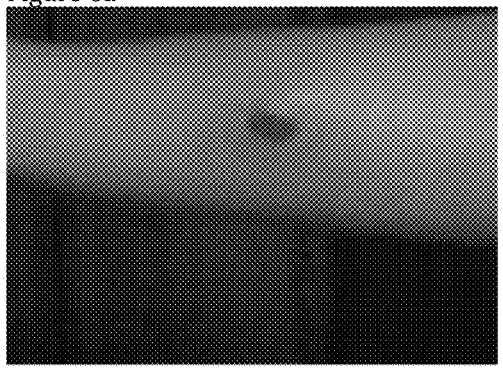
FIGS. 6a to 6f show the progress of treatment of Patient O.
Figure 6D:
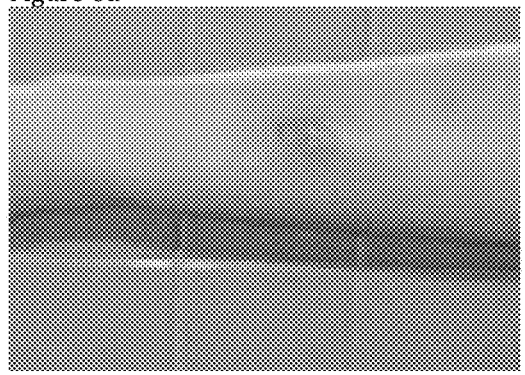
Figure 6B:
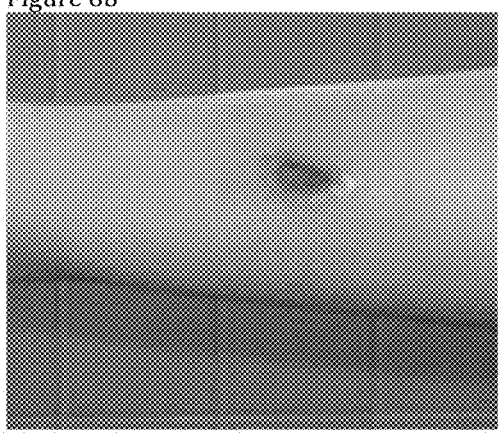
Figure 6E:
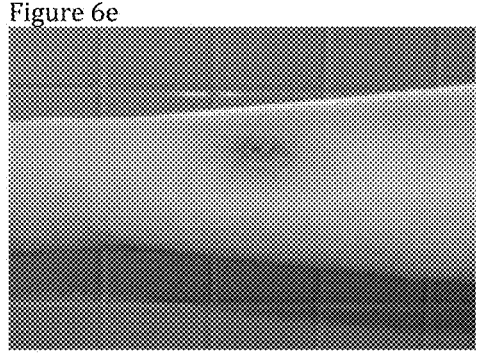
Figure 6C:
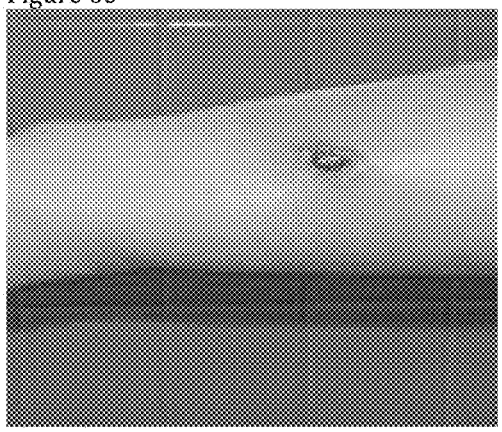
Figure 6F:
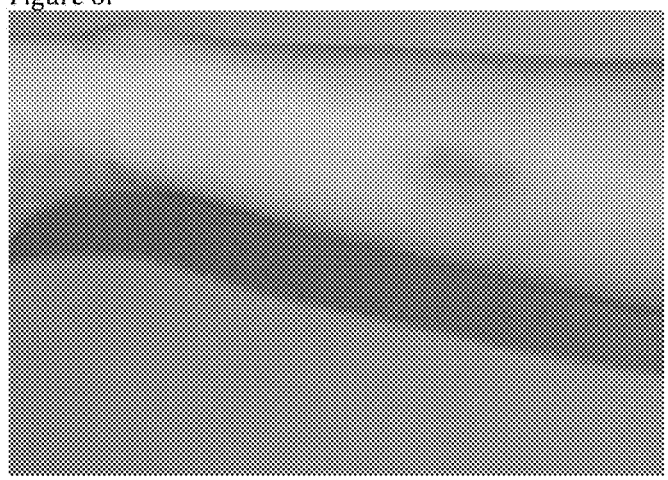

Further improvement at day 5 is documented in FIG. 5a, FIG. 5b shows the wound 9 days after first application of the composition, FIG. 5c shows the wound 10 days after first application of the composition, FIG. 5d shows the wound 11 days after first application of the composition, FIG. 5e shows the wound with further improvement after application of the composition.

FIG. 6 shows further improvement and the progress of treatment of Patient O; FIG. 6a shows the wound 16 days after first application of the composition, FIG. 6b shows the wound 18 days after first application of the composition, FIG. 6c shows the wound 21 days after first application of the composition, FIG. 6d shows the wound 30 days after first application of the composition, FIG. 6e shows the wound 31 days after first application of the composition, and FIG. 6f shows the wound 57 days after first application the composition.

Example 14

The following composition was used to test the effectiveness against various bacteria using the same procedures as described hereinabove, The formulation was about: 10%—Glycerol; 2.4% Glycerin; 3.6% Polysorbate 80; 4.2% White Petrolatum; 0.17% Citric Acid; 0.02% Trisodium Citrate; 0.6% Germazide; 32% SDBS 20% Solution; 0.03% Ascorbic Acid; 0.03% Magnesium Stearate; 0.03% Stearic Acid; 0.5%—Neomycin Sulfate; and qs to 100%—USP Purified Water.

| Bacteria | Zone of exclusion |
| --- | --- |
| E. coli | 15 MM |
| Staph. aureus | 24 MM |
| Pseudomonas aer. | 0 |
| Enterococci | 16 MM |
| Proteus vulgaris | 15 MM |
| Acetobacter | 16 MM |
| MRSA | 24 MM |
| Klebsiella | 15 MM |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An antimicrobial composition consisting of:
a safe and effective amount of sodium dodecylbenzene sulfonate at between 1 and 10% weight-to-weight and a safe and effective amount of ascorbic acid, wherein the composition of sodium dodecylbenzene sulfonate and ascorbic acid is antimicrobial against Methicillin-resistant *Staphylococcus aureus*.

2. The composition of claim 1, wherein the antimicrobial composition is effective to kill gram positive bacteria or multiple drug resistant bacteria.

3. An antimicrobial composition consisting of:
a safe and effective amount of sodium dodecylbenzene sulfonate, wherein the sodium dodecylbenzene sulfonate is in a concentration of 2 to 4%, 1 to 2%, 2 to 10%, 4% to 8%, 5% to 9%, 1%, 2%, 3%, 4%, 5%, 6%, 7%, 8%, 9% weight-to-weight and a safe and effective amount of ascorbic acid, wherein the composition of sodium dodecylbenzene sulfonate and ascorbic acid is antimicrobial against Methicillin-resistant *Staphylococcus aureus* and a safe and an effective amount of an antibiotic selected from the group consisting of bacitracin, bacitracin zinc, chlortetracycline hydrochloride, neomycin, clindamycin, erythromycin, or tetracycline hydrochloride, and mixture thereof.

4. An antimicrobial composition consisting of:
a safe and effective amount of sodium dodecylbenzene sulfonate, wherein the sodium dodecylbenzene sulfonate is in a concentration of 2 to 4%, 1 to 2%, 2 to 10%, 4% to 8%, 5% to 9%, 1%, 2%, 3%, 4%, 5%, 6%, 7%, 8%, 9% weight-to-weight and a safe and effective amount of ascorbic acid, wherein the composition of sodium dodecylbenzene sulfonate and ascorbic acid is antimicrobial against Methicillin-resistant *Staphylococcus aureus* and a safe and effective amount of stearic acid up to 1% weight-to-weight.

5. An antimicrobial composition consisting of:
a safe and effective amount of sodium dodecylbenzene sulfonate, wherein the sodium dodecylbenzene sulfonate is in a concentration of 2 to 4%, 1 to 2%, 2 to 10%, 4% to 8%, 5% to 9%, 1%, 2%, 3%, 4%, 5%, 6%, 7%, 8%, 9% weight-to-weight and a safe and effective amount of ascorbic acid, wherein the composition of sodium dodecylbenzene sulfonate and ascorbic acid is antimicrobial against Methicillin-resistant *Staphylococcus aureus* and a safe and effective amount of a biologically-compatible hypochlorite salt selected from the group consisting of sodium hypochlorite and calcium hypochlorite.

6. An antimicrobial composition consisting of:
a safe and effective amount of sodium dodecylbenzene sulfonate, wherein the sodium dodecylbenzene sulfonate is in a concentration of 2 to 4%, 1 to 2%, 2 to 10%, 4% to 8%, 5% to 9%, 1%, 2%, 3%, 4%, 5%, 6%, 7%, 8%, 9% weight-to-weight and a safe and effective amount of ascorbic acid, wherein the composition of sodium dodecylbenzene sulfonate and ascorbic acid is antimicrobial against Methicillin-resistant *Staphylococcus aureus* and a safe and effective amount of an abrasive material selected from the group consisting of sodium carbonate, sodium bicarbonate, calcium carbonate, sodium borate, silica, diatomaceous earth, cellulose-based materials, and mixture thereof.

7. An antimicrobial composition consisting of:
a safe and effective amount of sodium dodecylbenzene sulfonate at between 1 and 10% weight-to-weight;
a safe and effective amount of ascorbic acid, wherein the sodium dodecylbenzene sulfonate and the ascorbic acid are antimicrobial; and
a safe and effective amount of magnesium stearate, wherein the composition is antimicrobial against Methicillin-resistant *Staphylococcus aureus*.

8. The composition of claim 7, wherein the antimicrobial composition is effective to kill gram positive bacteria or multiple drug resistant bacteria.

9. An antimicrobial composition consisting of:
a safe and effective amount of sodium dodecylbenzene sulfonate, wherein the sodium dodecylbenzene sulfonate is in a concentration of 2 to 4%, 1 to 2%, 2 to 10%, 4% to 8%, 5% to 9%, 1%, 2%, 3%, 4%, 5%, 6%, 7%, 8%, 9% weight-to-weight;
a safe and effective amount of ascorbic acid, wherein the sodium dodecylbenzene sulfonate and the ascorbic acid are antimicrobial;
a safe and effective amount of magnesium stearate, wherein the composition of the sodium dodecylbenzene sulfonate and the ascorbic acid and the magnesium stearate is antimicrobial against Methicillin-resistant *Staphylococcus aureus*; and
a safe and effective amount of an antibiotic selected from the group consisting of bacitracin, bacitracin zinc, chlortetracycline hydrochloride, neomycin, clindamycin, erythromycin, or tetracycline hydrochloride, and mixture thereof.

10. An antimicrobial composition consisting of:
a safe and effective amount of sodium dodecylbenzene sulfonate, wherein the sodium dodecylbenzene sulfonate is in a concentration of 2 to 4%, 1 to 2%, 2 to 10%, 4% to 8%, 5% to 9%, 1%, 2%, 3%, 4%, 5%, 6%, 7%, 8%, 9% weight-to-weight;
a safe and effective amount of ascorbic acid, wherein the sodium dodecylbenzene sulfonate and the ascorbic acid are antimicrobial;
a safe and effective amount of magnesium stearate, wherein the composition of the sodium dodecylbenzene sulfonate and the ascorbic acid and the magnesium stearate is antimicrobial against Methicillin-resistant *Staphylococcus aureus*; and
a safe and effective amount of stearic acid up to 1% weight-to-weight.

11. An antimicrobial composition consisting of:
a safe and effective amount of sodium dodecylbenzene sulfonate, wherein the sodium dodecylbenzene sulfonate is in a concentration of 2 to 4%, 1 to 2%, 2 to 10%, 4% to 8%, 5% to 9%, 1%, 2%, 3%, 4%, 5%, 6%, 7%, 8%, 9% weight-to-weight;

a safe and effective amount of ascorbic acid, wherein the sodium dodecylbenzene sulfonate and the ascorbic acid are antimicrobial;

a safe and effective amount of magnesium stearate, wherein the composition of the sodium dodecylbenzene sulfonate and the ascorbic acid and the magnesium stearate is antimicrobial against Methicillin-resistant *Staphylococcus aureus*; and a biologically-compatible hypochlorite salt selected from the group consisting of sodium hypochlorite and calcium hypochlorite.

12. An antimicrobial composition consisting of:

a safe and effective amount of sodium dodecylbenzene sulfonate, wherein the sodium dodecylbenzene sulfonate is in a concentration of 2 to 4%, 1 to 2%, 2 to 10%, 4% to 8%, 5% to 9%, 1%, 2%, 3%, 4%, 5%, 6%, 7%, 8%, 9% weight-to-weight;

a safe and effective amount of ascorbic acid, wherein the sodium dodecylbenzene sulfonate and the ascorbic acid are antimicrobial;

a safe and effective amount of magnesium stearate, wherein the composition of the sodium dodecylbenzene sulfonate and the ascorbic acid and the magnesium stearate is antimicrobial against Methicillin-resistant *Staphylococcus aureus*; and an abrasive material selected from the group consisting of sodium carbonate, sodium bicarbonate, calcium carbonate, sodium borate, silica, diatomaceous earth, cellulose-based materials, and mixture thereof.

* * * * *